US010829822B2

(12) United States Patent
Chou et al.

(10) Patent No.: US 10,829,822 B2
(45) Date of Patent: Nov. 10, 2020

(54) METHOD FOR EVALUATING THE EFFICACY OF AN EGFR-TKI TREATMENT

(71) Applicant: LIHPAO LIFE SCIENCE CORP., New Taipei (TW)

(72) Inventors: Teh-Ying Chou, Taipei (TW); Chun-Ming Tsai, Taipei (TW)

(73) Assignee: LIHPAO LIFE SCIENCE CORP., New Taipei (TW)

( * ) Notice: Subject to any disclaimer, the term of this patent is extended or adjusted under 35 U.S.C. 154(b) by 121 days.

(21) Appl. No.: 16/138,244

(22) Filed: Sep. 21, 2018

(65) Prior Publication Data

US 2019/0010561 A1 Jan. 10, 2019

Related U.S. Application Data

(62) Division of application No. 14/643,197, filed on Mar. 10, 2015, now Pat. No. 10,106,856.

(60) Provisional application No. 61/950,288, filed on Mar. 10, 2014.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01); *C12Q 2600/158* (2013.01)

(58) Field of Classification Search
CPC .................................................. C12Q 1/6886
USPC .......................................................... 435/6.1
See application file for complete search history.

(56) References Cited

PUBLICATIONS

Fan et al (Clin Cancer Res, 2007, 13(24): 7515-7521).*
Kato et al (Biochemical and Biophysical Research Communications, 2013, 432: 564-567).*
Maeng et al (PLoS One, 2012, 7(8): 1-5).*
Kim Y. M. et al., BMB Reports, 2010; 43(10): 693-697.
Kim, J. C. et al. Familial Cancer 3: 129-137, 2004.
Lo Y.-L et al., Lung Cancer 72 (2011) 280-286.
Raptis, S. et al., JNCO, vol. 99, Issue 6, Mar. 21, 2007, p. 463-474 (Year: 2007).
Sakiyama T. et al., Int. J. Cancer: 114, 730-737 (2005) (Year: 2005).

* cited by examiner

*Primary Examiner* — Sean E Aeder
(74) *Attorney, Agent, or Firm* — Birch, Stewart, Kolasch & Birch, LLP.

(57) ABSTRACT

The present invention provides a method for evaluating the efficacy of an EGFR-TKI treatment to a subject, comprising identifying the V384D mutation in said subject. By identifying said mutation, the efficacy of the EGFR-TKI treatment and the progression-free survival of said subject after treatment can be estimated.

3 Claims, 12 Drawing Sheets

Specification includes a Sequence Listing.

METHOD FOR EVALUATING THE EFFICACY OF AN EGFR-TKI TREATMENT

CROSS REFERENCE TO RELATED APPLICATIONS

This application is a Divisional of co-pending U.S. application Ser. No. 14/643,197 filed on Mar. 10, 2015, which claims priority to Provisional Application No. 61/950,288 filed on Mar. 10, 2014. The entire contents of each of these applications are hereby incorporated by reference.

BACKGROUND

Technical Field

The present invention relates to a method for evaluating the efficacy of a cancer therapy. More specifically, the present invention relates to a method for evaluating the efficacy of an EGFR-TKI treatment and estimating the progression-free survival of a subject.

REFERENCE TO SEQUENCE LISTING SUBMITTED VIA EFS-WEB

This application includes an electronically submitted sequence listing in .txt format. The .txt file contains a sequence listing entitled "20170201_50250234PUS2_ST25.txt" created on Feb. 1, 2017 and is 88,974 bytes in size. The sequence listing contained in this .txt file is part of the specification and is hereby incorporated by reference herein in its entirety.

Description of Related Art

Lung cancer has high incidence rates worldwide, and its 5-year survival is dismal as most cases are diagnosed at late stages. Chemotherapy, although with limited efficacy, used to be the main treatment option for patients with advanced lung cancer. In 2004, somatic mutations were reported to exist in the tyrosine kinase domain of epidermal growth factor receptor (EGFR) in tumors of a subset of patients with non-small cell lung cancer (NSCLC) who responded dramatically to EGFR tyrosine kinase inhibitors (TKIs). This discovery has opened a new era of targeted therapy for NSCLC. Nowadays, EGFR-TKIs are used as the standard first-line therapy for patients with advanced lung adenocarcinoma harboring activating EGFR mutations, and they remarkably improve the survival and quality of life in patients with these driver mutations.

Drug resistance is a major obstacle in targeted cancer therapy, and understanding the mechanisms of resistance is pivotal for developing more effective treatment strategies. Around 70% of patients with lung adenocarcinoma that has activating EGFR mutations (mostly a small in-frame deletion in exon 19 and a substitution mutation L858R) display objective clinical response to EGFR-TKI treatment. However, despite the initial disease control, tumor relapse is inevitably observed after a median of 9-14 months, indicating the development of acquired resistance to EGFR-TKIs in these patients. Studies have identified different mechanisms of acquired EGFR-TKI resistance, including a second-site EGFR T790M mutation, MET amplification, PIK3CA mutations, epithelial-to-mesenchymal transitions and conversion to small cell carcinoma. On the other hand, ~30% patients with TKI-sensitive EGFR mutations fail to demonstrate objective tumor regression on initial EGFR-TKI therapy and are defined as having primary or intrinsic resistance. Some co-existing genetic variations have been implicated in the mechanism of TKI insensitivity in EGFR-mutant patients, including de novo presence of EGFR T790M or MET amplification, KRAS mutations, loss of PTEN, and a germline deletion polymorphism of BIM. However, the majority of resistant cases cannot be explained by these variations and the mechanistic basis for intrinsic EGFR-TKI resistance in patients supposed to be responsive is still largely unknown.

In light of the high death rate of cancer and the expensive cost for cancer therapy (especially, targeted therapy), there is continuously a need for a method for evaluating the efficacy of an EGFR-TKI treatment before or after the treatment.

SUMMARY

In light of the foregoing, one of the objects of the present invention is to provide a method for evaluating the efficacy of an EGFR-TKI treatment so that the patients in need can be screened before the treatment to prevent from investing costs in ineffective therapy.

Another object of the present invention is to provide a method for evaluating a progression-free survival of a subject so that the follow-up treating strategies can be set up as soon as possible after an EGFR-TKI treatment.

In order to achieve the above-mentioned objects, the present invention provides a method for evaluating the efficacy of an EGFR-TKI treatment to a subject, comprising: (A) providing a sample from said subject; (B) analyzing a sequence of MLH1 DNA, a sequence of MLH1 mRNA, and/or a cDNA sequence from said MLH1 mRNA of said sample, to identify an alteration at V384 of an encoded MLH1 protein; or analyzing a MLH1 protein of said sample to identify an alteration at V384 of said MLH1 protein; provided that when said alteration is identified, a response rate of said subject to said EGFR-TKI treatment is from 0% to 50%; or provided that when said alteration is identified, said progression-free survival of said subject is 1.5 to 8.7 months; whereas, when said alteration is not identified, said progression-free survival of said subject is 8.8 to 12.5 months.

Preferably, said alteration at V384 is V384D.

Preferably, said alteration corresponds with a T1349 mutation of said MLH1 mRNA. Preferably, said T1349 mutation is a T1349A mutation.

Preferably, said alteration corresponds with a T1151 mutation of said cDNA.

Preferably, said TI 151 mutation is a T1151A mutation.

Preferably, said analyzing is performed by polymerase chain reaction, Southern blot, Western blot, or a combination thereof.

Preferably, said analyzing is performed by using an antibody, a primer set, a probe, or a combination thereof.

Preferably, said method is conducted before and/or after said EGFR-TKI treatment.

The present invention also provides a method for estimating a progression-free survival of a subject, comprising: (A) providing a sample from said subject; (B) analyzing a sequence of MLH1 DNA, a sequence of MLH1 mRNA, and/or a cDNA sequence from said MLH1 mRNA of said sample, to identify an alteration at V384 of an encoded MLH1 protein; or analyzing a MLH1 protein of said sample to identify an alteration at V384 of said MLH1 protein; provided that when said alteration is identified, said progression-free survival of said subject is 1.5 to 8.7 months; or when said alteration is not identified, said progression-free survival of said subject is 8.8 to 12.5 months.

Preferably, said alteration at V384 is V384D.

Preferably, said alteration corresponds with a T1151 mutation of said MLH1 mRNA. Preferably, said T1151 mutation is a T1151A mutation.

Preferably, said alteration corresponds with a T1151 mutation of said cDNA.

Preferably, said TI 151 mutation is a T1151A mutation.

Preferably, said analyzing is performed by polymerase chain reaction, Southern blot, Western blot, or a combination thereof.

Preferably, said analyzing is performed by using an antibody, a primer set, a probe, or a combination thereof. Preferably, said primer set comprises SEQ ID NO: 05 and SEQ ID NO: 06.

Preferably, said subject has been treated with an EGFR-TKI treatment.

Preferably, said subject suffers from lung cancer or is suspected to suffer from lung cancer.

To sum up, the present invention identifies the correlation between the MLH1 V384D mutation with the poor efficacy and short progression-free survival of an EGFR-TKI treatment. By applying this information in evaluating the efficacy of an EGFR-TKI treatment before or after treatment and in estimating a progression-free survival of a subject can provide better treating strategies for patients in need.

DETAILED DESCRIPTION

Figure 1A:
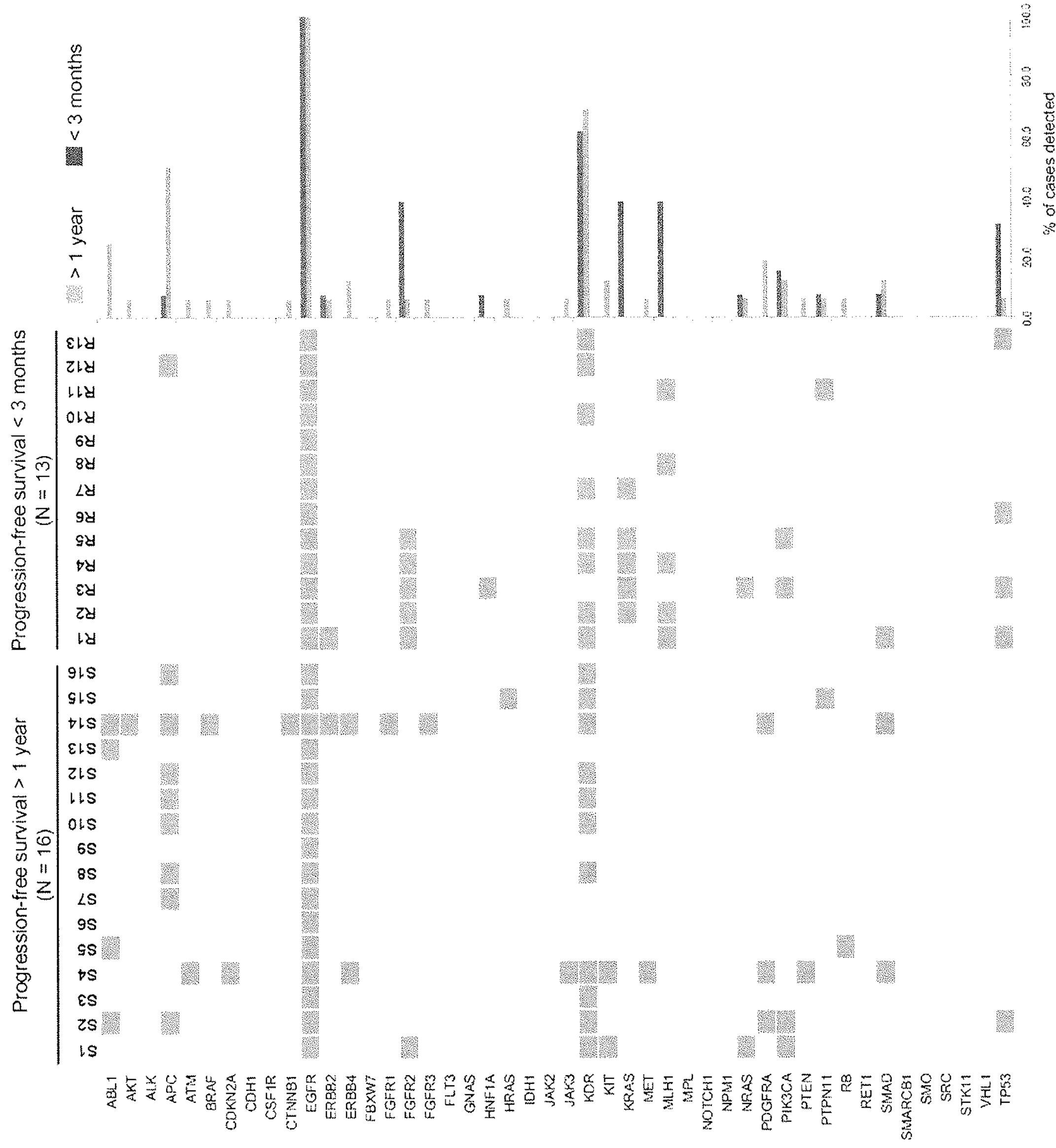
FIG. 1A shows the results of Next-Generation Sequencing in Example 2 for comparing patients having PFS >1 year (N=16) with patients having PFS <3 months (N=13).

In this study, we hypothesized that specific genetic alterations may underlie the primary resistance to EGFR-TKIs in lung adenocarcinoma harboring activating EGFR mutations. Towards uncovering such genetic determinants of treatment resistance, we performed Next-Generation Sequencing (NGS)-based mutation profiling of lung adenocarcinoma with the EGFR L858R mutation from patients who received EGFR-TKI therapy, and searched for genetic variants/mutations that could differentiate patients displaying primary resistance to EGFR-TKIs from those having a durable response.

The term of "EGFR-TKI therapy" or "EGFR-TKI treatment" used herein is referred to as a targeted therapy or targeted treatment adopting the fact that a fair amount of non-small cell lung cancer patients share a somatic mutation in the tyrosine kinase domain of epidermal growth factor receptor of tumor cells. Specifically, the "EGFR-TKI therapy" or "EGFR-TKI treatment" is conducted by using an EGFR tyrosine kinase inhibitor targeting the somatic mutation in the tyrosine kinase domain of epidermal growth factor receptor of tumor cells.

The term of "efficacy of an EGFR-TKI treatment" used herein is referred to as the effect of an EGFR-TKI treatment on the progression of tumors. The "efficacy of an EGFR-TKI treatment" can be determined by the response rate of the patient concerned to said EGFR-TKI treatment. After being treated by EGFR-TKI treatment, if the tumor size of the patient decreased at least 20% from the initial size there of before treatment in 3 months, the patient is deemed as response to the treatment. The response rate can be calculated by the number of patients having response out of the total number of the patient monitored.

The other way to determine the efficacy of an EGFR-TKI treatment is by observing the "progression-free survival" of the patient concerned. The term of "progression-free survival" used herein is referred to as the time period between the initial date of a treatment and the time point that the tumor concerned begins to progress again. In other words, it is the length of time that the tumors, during this time period, have no progression or are reduced in size.

The term of "analyzing" or "analyze" used herein is referred to as evaluating or examining a property of a subject of interest by at least of technical means. Said technical means include but not limited to polymerase chain reaction, Southern blot, and Western blot.

The term of "V384" used herein is referred to as the $384^{th}$ amino acid of the amino acid sequences of MLH1 protein; wherein "V" is the one-letter abbreviation of Valine (Val). The term of "alteration at V384" used herein is referred to as the $384^{th}$ amino acid of Valine is altered to another amino acid other than Valine. The term of "alteration at V384D" used herein is referred to as the $384^{th}$ amino acid of Valine is altered to Aspartic acid; wherein "D" is the one-letter abbreviation of Aspartic acid (Asp). See also SEQ ID NO: 01 for the amino acid sequence having the aforesaid mutation and SEQ ID NO: 02 for the DNA sequence having the aforesaid mutation.

The term of "T1349" used herein is referred to as the $1349^{th}$ nucleotide of the nucleotide sequence of a mRNA encoding a MLH1 protein; "T" is an abbreviation of thymine. The term of "T1349 mutation" used herein is referred to as the $1349^{th}$ nucleotide of thymine is altered/mutated to another nucleotide other than thymine. The term of "alteration at T1349A" used herein is referred to as the $1349^{th}$ nucleotide of thymine is altered to adenine; wherein "A" is an abbreviation of adenine. See also SEQ ID NO: 03 for the mRNA sequence having the aforesaid mutation.

The term of "T1151" used herein is referred to as the $1151^{th}$ nucleotide of the nucleotide sequence of a cDNA; wherein said cDNA is from a mRNA encoding a MLH1 protein; "T" is an abbreviation of thymine. The term of "T1151 mutation" used herein is referred to as the $1151^{th}$ nucleotide of thymine is altered/mutated to another nucleotide other than thymine. The term of "alteration at T1151A"

used herein is referred to as the 1151$^{th}$ nucleotide of thymine is altered to adenine; wherein "A" is an abbreviation of adenine. See also SEQ ID NO: 04 for the cDNA sequence having the aforesaid mutation.

The present invention identifies the correlation between the mutation at V384 of MHL1 with the poor efficacy of EGFR-TKI treatment of a patient.

In one aspect of the present invention, a method for evaluating the efficacy of an EGFR-TKI treatment to a subject is provided. In another aspect of the present invention, a method for estimating a progression-free survival of a subject is provided.

The method for evaluating the efficacy of an EGFR-TKI treatment to a subject comprises (A) providing a sample from said subject; and (B) analyzing a sequence of MLH1 DNA, a sequence of MLH1 mRNA, and/or a cDNA sequence from said MLH1 mRNA of said sample, to identify an alteration at V384 of an encoded MLH1 protein; or analyzing a MLH1 protein of said sample to identify an alteration at V384 of said MLH1 protein; provided that when said alteration is identified, a probability that said EGFR-TKI treatment has efficacy to said subject is from 0% to 50%; or provided that when said alteration is identified, said progression-free survival of said subject is 1.5 to 8.7 months; or when said alteration is not identified, said progression-free survival of said subject is 8.8 to 12.5 months.

Said sample is collected from a subject concerned and it could be from tumor tissues or blood of said subject. Said subject may be a patient suffering from cancer (preferably, non-small cell lung cancer). In an alternative embodiment of the present invention, the aforesaid methods can be conducted before or after an EGFR-TKI treatment. Preferably, the aforesaid methods are conducted before an EGFR-TKI treatment so that the aforesaid methods are served as a pre-evaluation for testing if the subject is suitable for the EGFR-TKI treatment. In this way, the cost for the EGFR-TKI treatment can be saved (if the subject concerned is found not suitable for the EGFR treatment) and proper treating strategies can be set up as earlier as possible.

In an alternative embodiment, the mutation at V384 may be an alteration of Valine to any other amino acid. Correspondingly, the nucleotide sequence of the mRNA encoding the MLH1 protein at the V384 position may be altered from GUU, GUC, GUA, or GUG to any codon other than GUU, GUC, GUA, or GUG. Also, the nucleotide sequence of the cDNA from said mRNA encoding the MLH1 protein at the V384 position may be correspondingly altered from GTT, GTC, GTA, or GTG to any codon other than GTT, GTC, GTA, or GTG.

In a preferable embodiment, the mutation at V384 of MHL1 is an alteration of Valine to Aspartic acid. Correspondingly, the nucleotide sequence of said mRNA is altered to GAU or GAC. Also, the nucleotide sequence of said cDNA is correspondingly altered to GAT or GAC.

The aforesaid alteration of V384 can be detected by Western blot via a suitable antibody. In an alteration embodiment, the alteration of V384 can be detected by analyzing the DNA, mRNA, or cDNA of MLH1 via polymerase chain reaction, Southern blot, or any well-understood technical manners in the art; wherein a suitable primer set or probe can be used in the analysis.

Example 1: Research Preparation

[Patients and Study Design]

Patients were included if they had primary lung adenocarcinoma harboring the L858R mutation without a co-existing T790M mutation in EGFR and received their first-time EGFR-TKI treatment at Taipei Veterans General Hospital during the period from January 2009 to January 2013. Patients who had prior EGFR-TKI therapy or received EGFR-TKI in combination with other anti-cancer treatment were excluded. Patients who had adequate tumor specimens for further molecular testing were enrolled. This study was approved by the Institution Review Board of Taipei Veterans General Hospital.

The size of the tumor is monitored for at least two months after the initiation of EGFR-TKI therapy and usually measured approximately three months after the initiation of treatment. If tumors progressed within the aforesaid period, we considered that the treatment was clinically ineffective and that these patients presented primary (or intrinsic) resistance. To discover candidate genetic variations that may associate with primary EGFR-TKI resistance in EGFR mutant tumors, we performed genomic profiling of EGFR L858R tumors from 16 patients with long (>1 year) progression-free survival (PFS) and 13 patients with short (<3 months) PFS. NGS was performed to screen through a cancer-related gene mutation panel (Ion AmpliSeq Cancer Panel, Ion Torrent, Life Technologies); 739 mutation hotspot regions within 46 key cancer-related genes from the COSMIC database were examined. Distributions of genomic variants in the two groups of patients were compared. Genes with differential mutation status between two groups were further investigated in a total of 158 EGFR L858R tumors by PCR amplification and direct Sanger sequencing, and the association of candidate variants with differential tumor response to EGFR-TKIs was explored.

[Histopathology Review and Sample Preparation]

Consecutive tissue sections were prepared from each archived formalin-fixed paraffin-embedded (FFPE) pathology specimen and reviewed by pathologists; tumor areas were marked on deparaffinized unstained sections and manually dissected. Proteinase K-digested tissue extracts were subjected to genomic profiling tests. Genomic DNA was also prepared from available blood samples using the illustra blood genomicPrep Mini Spin Kit (GE Healthcare Life Sciences) according to the manufacturer's protocol.

[Statistical Analysis]

The objective tumor response was evaluated according to the revised RECIST criteria. PFS was calculated from the date of starting EGFR-TKI therapy to the date of disease progression or death. The association between patient characteristics and MLHJ mutation status was analyzed by chi-square and Fisher's exact tests. Kaplan-Meier survival curves were constructed and compared using the log-rank test. Cox regression models were built using a backward stepwise procedure for multivariate survival analysis. Analyses were carried out using PASW Statistics 18.0 (SPSS Inc., Chicago, Ill.)

Example 2: Forty-Six-Gene Mutation Profiles of EGFR L858R-Positive Lung Adenocarcinomas Next-generation sequencing (NGS) was used to interrogate mutations within hotspot regions of 46 cancer-related genes in lung adenocarcinoma samples from 13 and 16 EGFR-TKI-treated patients who had short (<3 months) and long (>1 year) PFS, respectively.

[Next-Generation Sequencing]

Genomic DNA from FFPE tumor tissues was quantified using the Qubit® dsDNA HS Assay Kit and the Qubit® fluorometer (Life Technologies); 10 nanograms were amplified by multiplex PCR using the Ion AmpliSeq Cancer Panel Primers Pool (Life Technologies). PCR amplicons were ligated with barcode adaptors using the Ion Xpress Barcode Adapters 1-16 Kit (Life Technologies), and subjected to emulsion PCR. Template was prepared by the automated Ion OneTouch System using the Ion OneTouch 200 Template Kit v2 DL, and DNA was sequenced on a 316 chip using the Ion PGM Sequencing Kit v2 and the Ion Torrent Personal Genome Machine (PGM, Ion Torrent, Life Technologies). Data were analyzed using the Torrent Suite software v3.0 and the Ion Torrent Variant Caller software v3.0. Variants were called when a minimum coverage of 500 reads was achieved and at least 5% of variant reads were identified.

[Results]

Figure 1B:
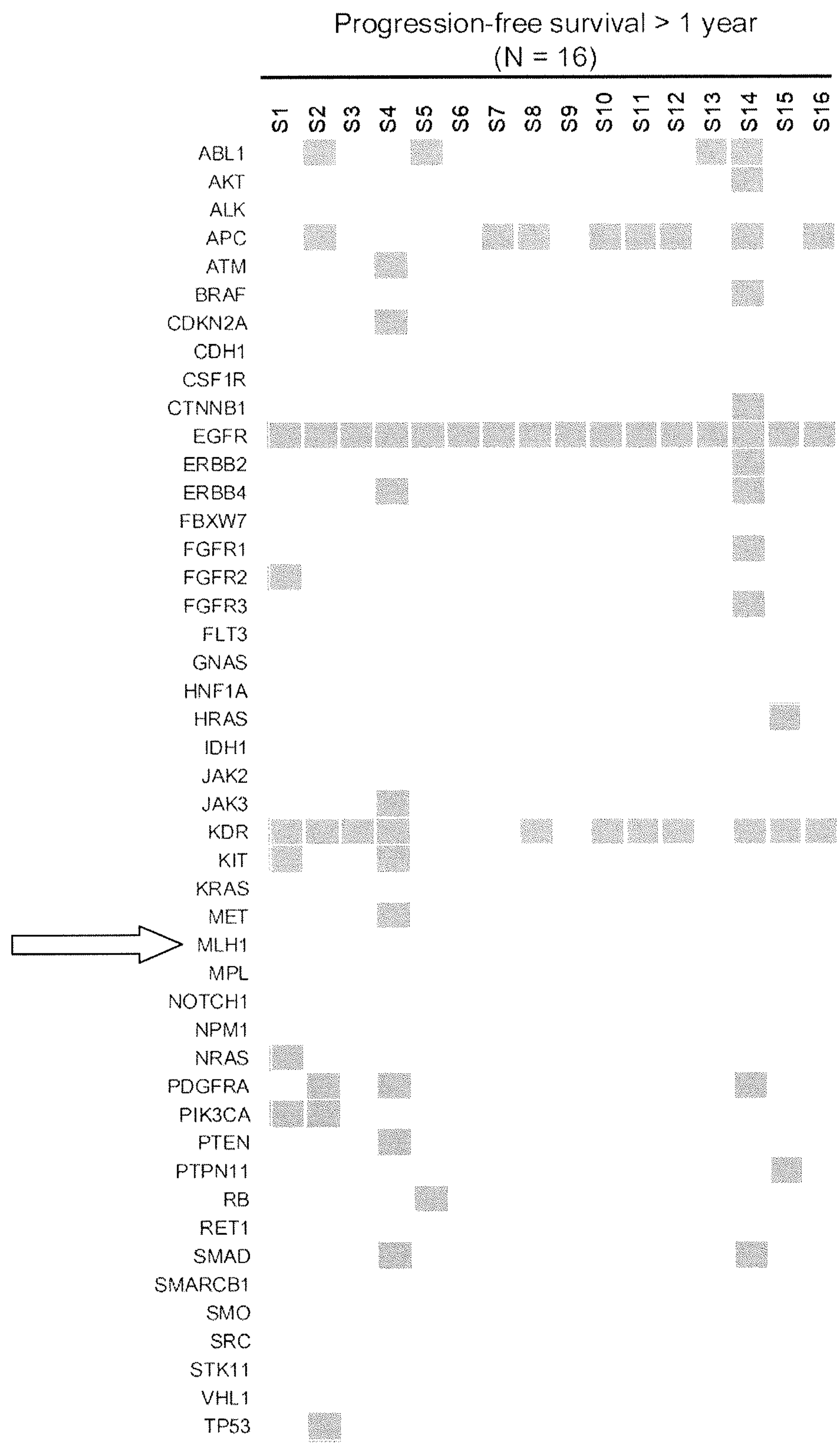
FIG. 1B shows the magnified image of the left chart of FIG. 1A (patients having PFS >1 year).
Figure 1C:
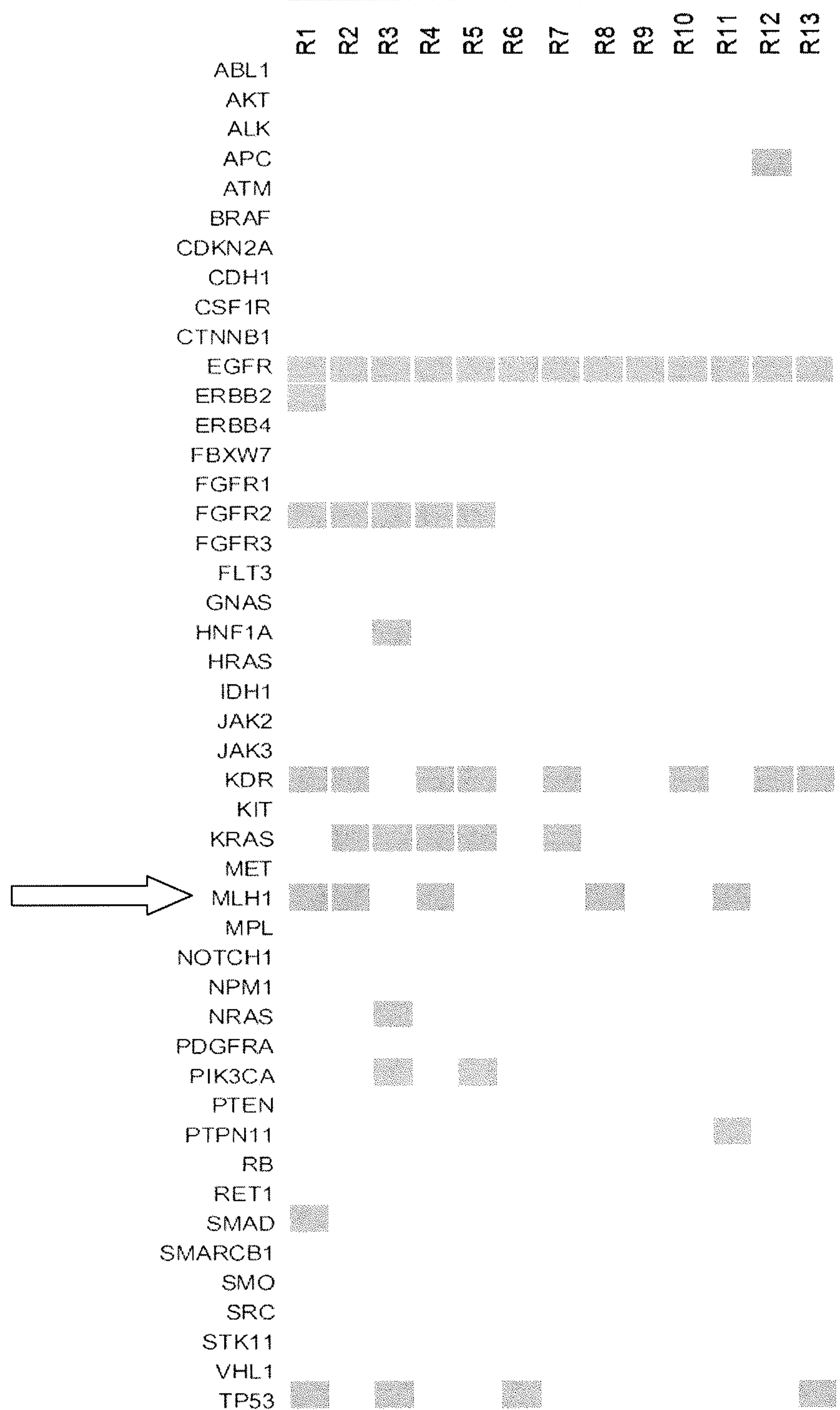
FIG. 1C shows the magnified image of the middle chart of FIG. 1A (patients having PFS <3 months).
Figure 1D:
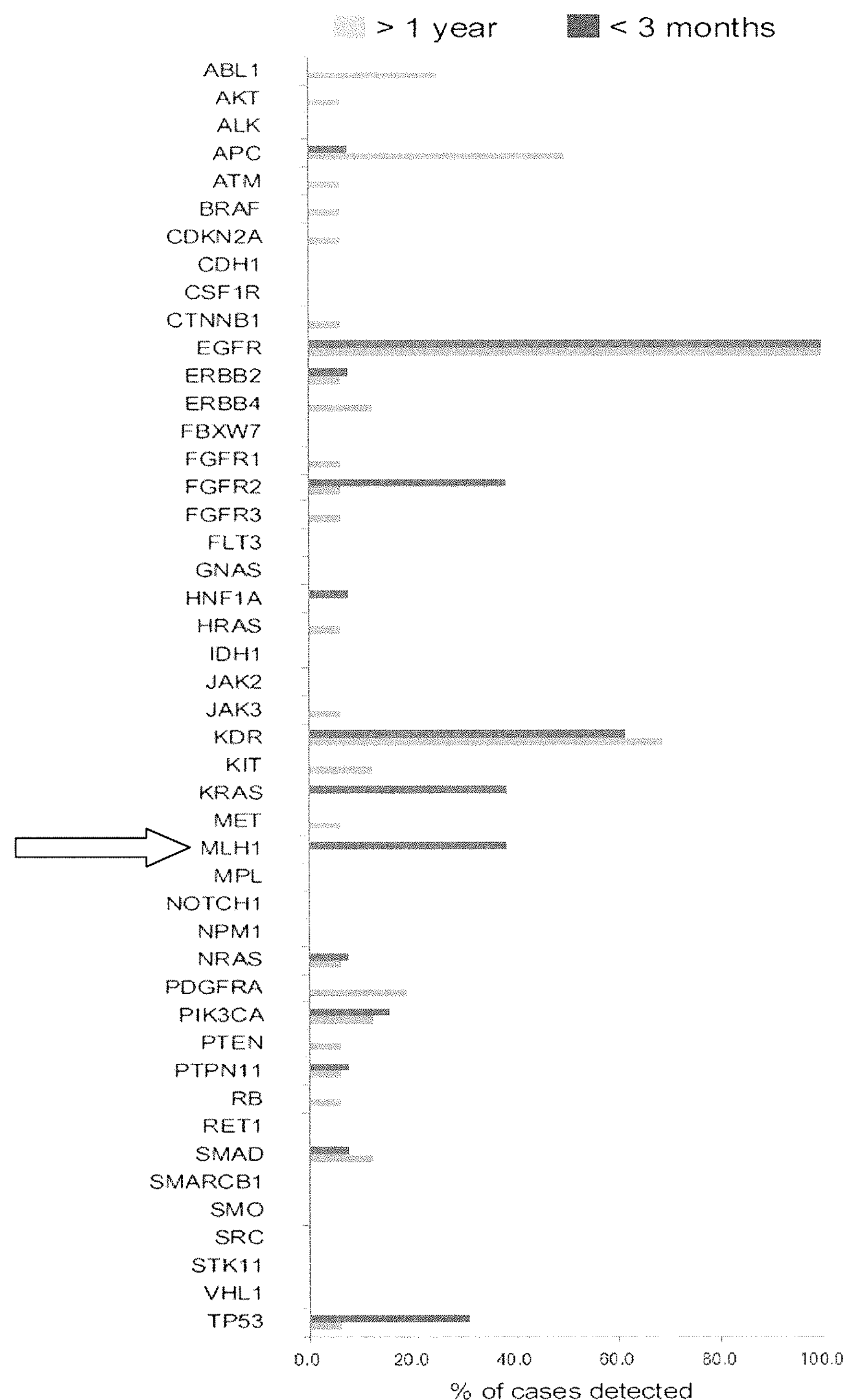
FIG. 1D shows the magnified image of the right chart of FIG. 1A (the bar chart).
Figure 1E:
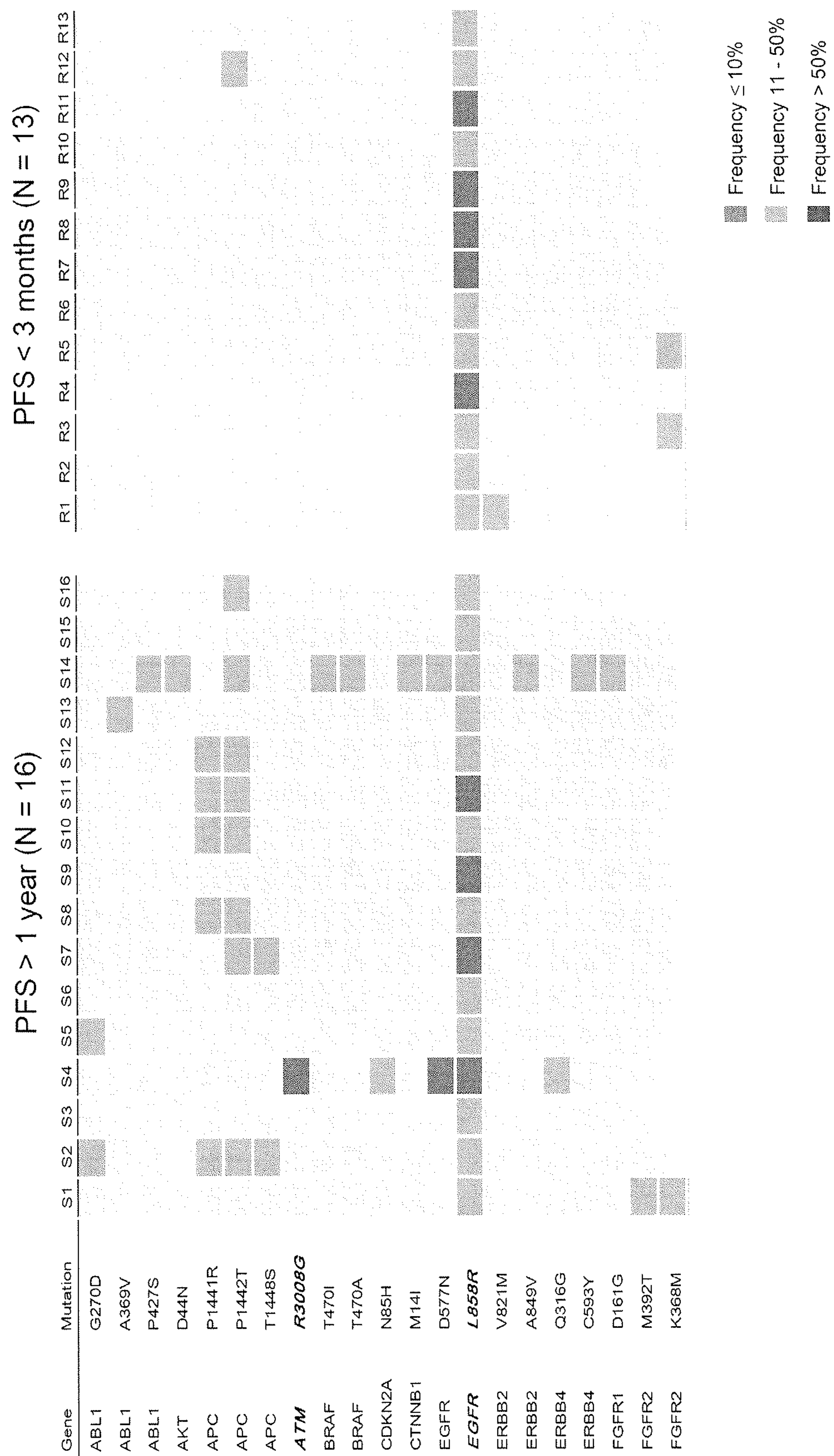
FIG. 1E shows more details of the results of the Next-Generation Sequencing in Example 2, including the mutation of the listing genes and the frequency thereof.
Figure 1E:
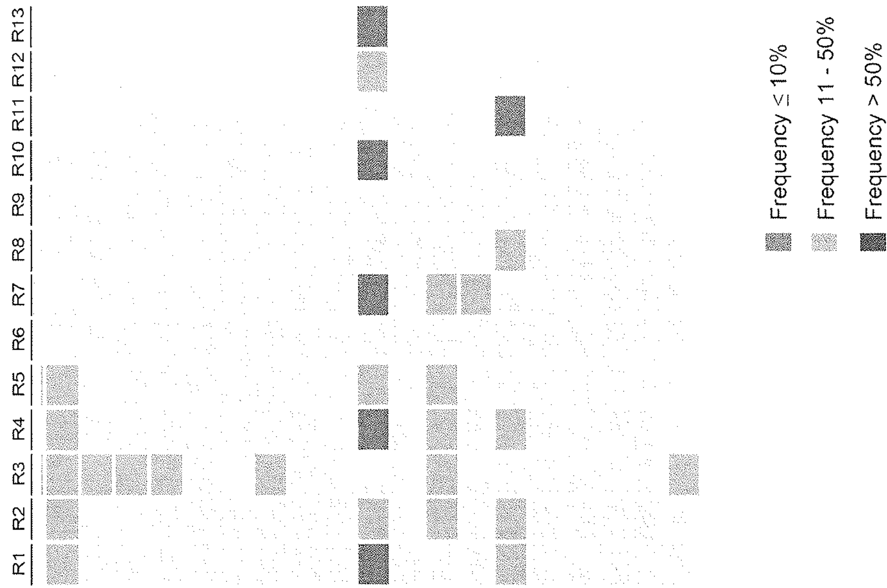
Figure 1E:
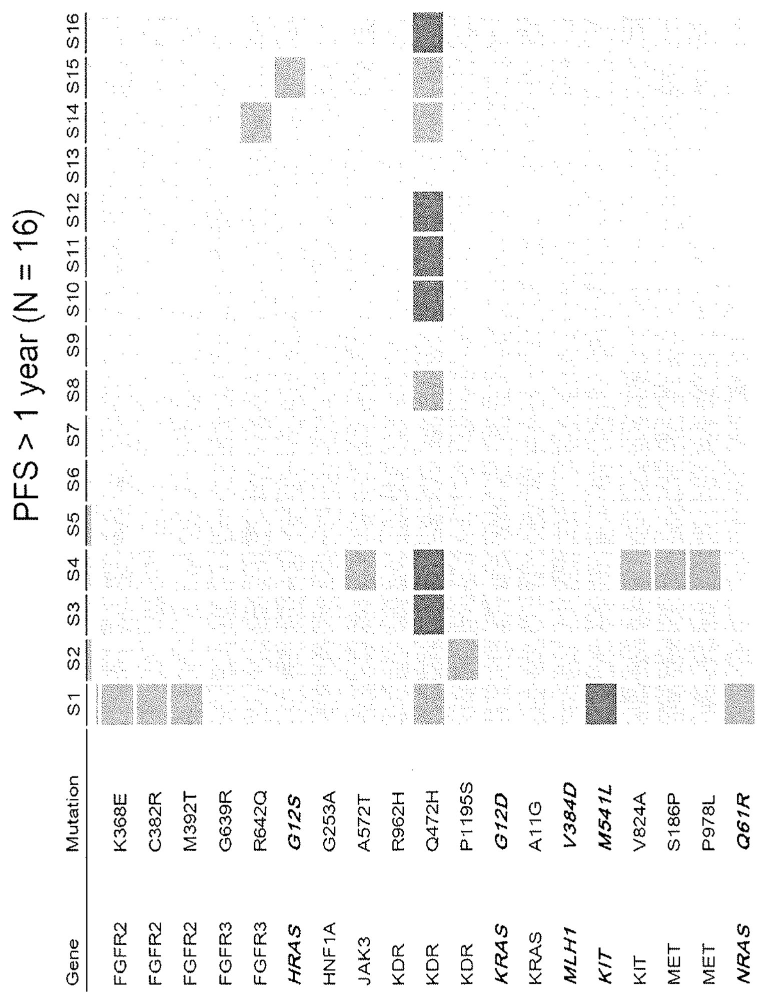
Figure 1E:
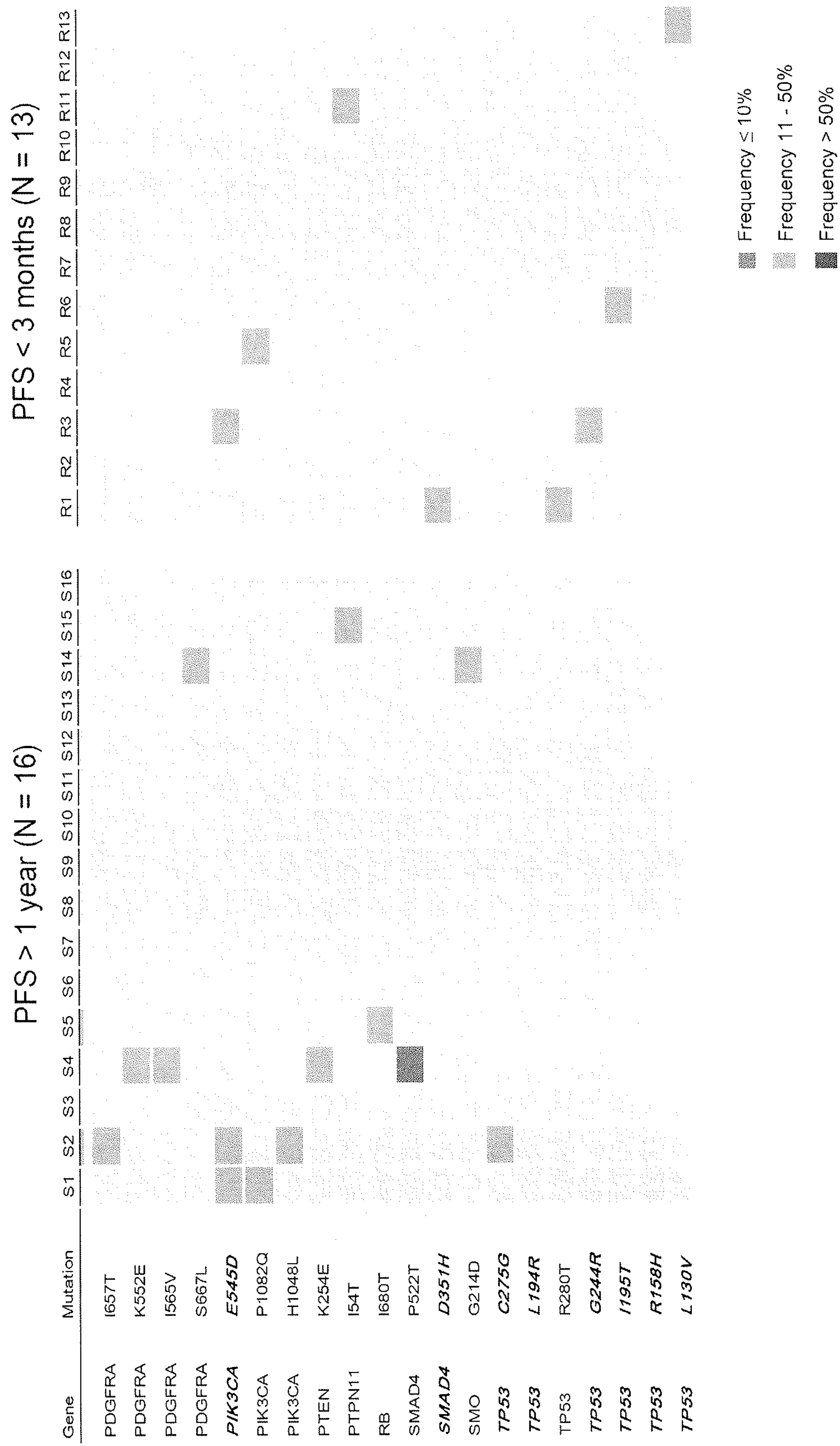

The results were show in FIG. 1A and more details in FIG. 1E. Moreover, the results showed in FIG. 1A were magnified and separately shown in FIGS. 1B, 1C and 1D.

Differential mutation patterns were revealed in these two groups (that is, long PFS and short PFS). All 29 tumors (16 patients with long (>1 year) PFS and 13 patients with short (<3 months) PFS) were confirmed to harbor the activating EGFR L858R mutation without the simultaneous presence of the T790M allele that predicts EGFR-TKI resistance. Among the 46 genes, KDR (which encodes for vascular endothelial growth factor receptor 2) was the most commonly mutated gene coexisting with EGFR L858R, regardless of the patient's treatment response. Mutation rates of ABL1, APC, and PDGFRA were disproportionately high in the patient with long PFS. In contrast, mutations in FGFR2 (K368E), KRAS (G12D), MLH1 (V384D), and TP53 occurred more often in patients with short PFS. Derepression of FGFR2 expression has been implicated in the mechanism for rapidly acquired EGFR-TKI resistance in NSCLC cells. KRAS G12C is linked to poor outcomes of EGFR-TKI therapy in NSCLC patients.

With regard to FIG. 1E, amino acids variations within the hotspot regions of 46 cancer-related genes in individual EGFR L858R tumors are shown on the left in 2 groups, according to the progression-free survival (PFS) of patients. Frequencies of individual genetic variations detected by the IonTorrent software were grouped into three ranges and shown in different colors. Variations shown in bold and italic are hotspot mutations published in the COSMIC database.

The results shown in FIGS. 1A, 1B, 1C, 1D and 1E indicates the association between the DNA mismatch repair gene MLH1 and EGFR-TKI resistance, which was never known before the present research.

Example 3: MLH1 V384D in Patients with Primary Lung Adenocarcinoma

In this example, a total of 158 tumors were subjected to MLH1 mutation analysis by direct sequencing of PCR products for examining the mutation status of MLH1 in a larger set of EGFR L858R-positive lung adenocarcinomas.

[PCR and Sanger Sequencing]

Exon 12 of the MLH1 gene was amplified from genomic DNA by PCR using a forward primer (SEQ ID NO: 05: 5'-CAGACTTTGCTACCAGGACTTGC-3') and a reverse primer (SEQ ID NO: 06: 5'-CTGCCTAGCCCTGCCACTAG-3'). PCR products were sequenced using the Sanger method. DNA sequences were analyzed by the Mutation Surveyor software (SoftGenetics, State College, Pa.).

[Results]

Figure 2:
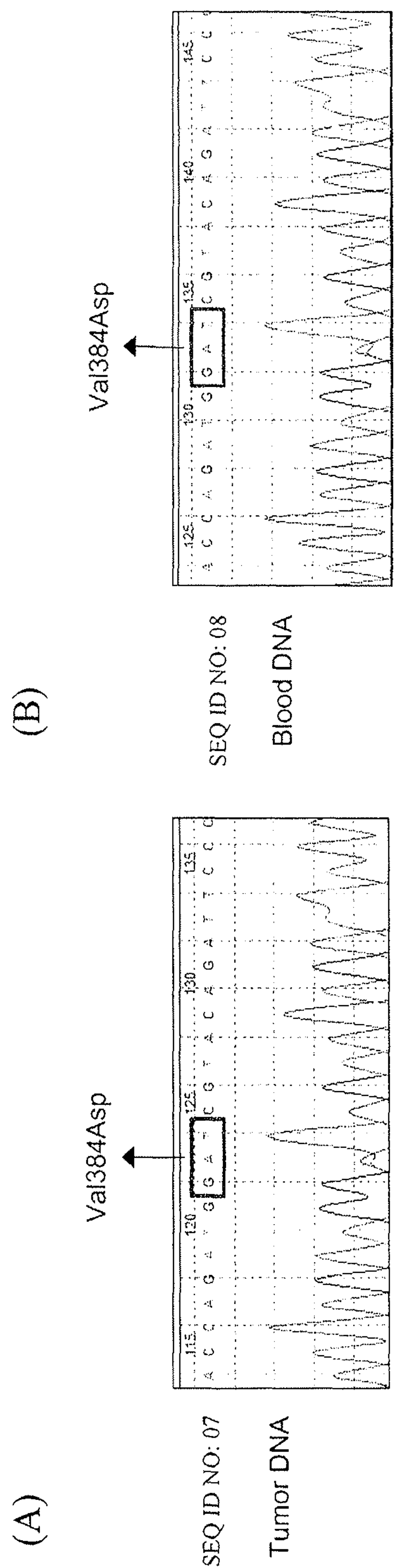
FIG. 2 shows the results of Sanger sequencing in Example 3, which indicates the mutation of V384D. (A) (SEQ ID NO: 7) DNA from tumor sample. (B) (SEQ ID NO: 8) DNA from blood sample.

Fourteen of the 158 tumors (8.9%) had a heterozygous change at nucleotide 1151 (FIGS. 2A and 2B) which results in the same V384D substitution in MLH1 as discovered in NGS screening. We were able to analyze genomic DNA from blood specimens of 4 patients and non-tumor tissue specimens from 1 patient, and all of these samples were tested positive for MLH1 V384D (FIG. 2B). Clinical characteristics of patients with or without MLH1 V384D were analyzed (Table 1), and no statistically significant demographic differences between the two groups were noted. We also performed sequencing analysis of MLH1 exon 12 in 51 EGFR-wildtype lung adenocarcinomas and found a comparable incidence (4/51, 7.8%) of the MLH1 V384D allele.

TABLE 1

| Patient characteristics (n = 158) | | | |
|---|---|---|---|
| | MLH1 codon 384 | | |
| | V/V | V/D | P value |
| Total case number | 144 | 14 | |
| Gender | | | 0.577 |
| Male | 50 | 5 | |
| Female | 94 | 9 | |
| Age | | | 0.240 |
| Median | 65 | 60 | |
| (Range) | (38-94) | (43-78) | |
| Smoking | | | 0.096 |
| Never | 111 | 8 | |
| Ever | 33 | 6 | |
| Stage | | | 0.119 |
| IIIB | 5 | 2 | |
| IV | 139 | 12 | |
| Number of prior chemotherapy | | | 0.661 |
| 0 | 116 | 12 | |
| 1 | 24 | 2 | |
| 2 | 4 | 0 | |
| EGFR mutation | | | 0.756 |
| L858R | 141 | 14 | |
| L858R. complex | 3 | 0 | |
| EGFR-TKI | | | 0.897 |
| Gefitinib | 120 | 12 | |
| Erlotinib | 23 | 2 | |
| Afatinib | 1 | 0 | |

Example 4: Tumor Response to EGFR-TKI

Figure 3:
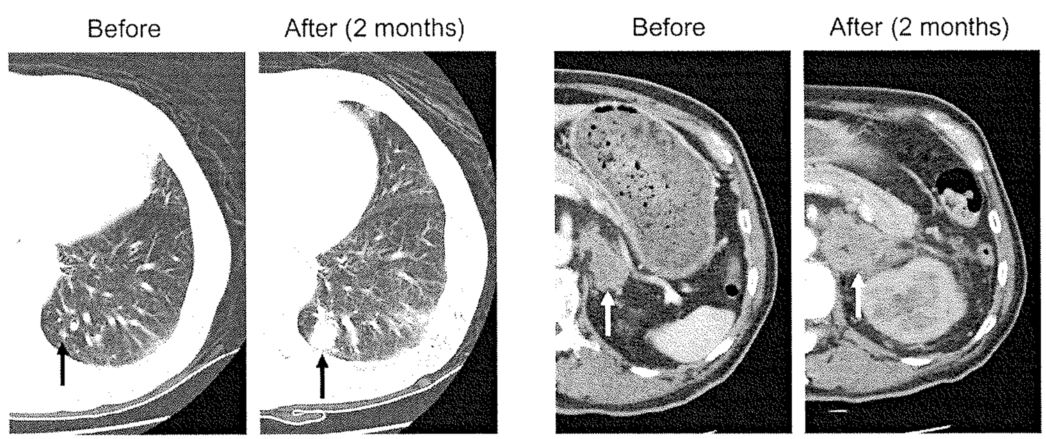
FIG. 3 shows images of chest CT scans of lung (black arrow) and adrenal gland (white arrow) metastases of a lung cancer patient with MLH1 V384D mutation before and after Erlotinib (Tarceve) treatment.

In this example, a patient with MLH1 V384D mutation was monitored for two months after being treated with Erlotinib (Tarceva) (a commercial EGFR-TKI drug). The chest CT scans (FIG. 3) of the patient showed that lung (black arrow) and adrenal gland (white arrow) metastasis remained persistent growth after treatment. The observation indicates the poor efficacy of EGFR-TKI therapy in patients with MLH1 V384D mutation. The response rate was calculated by the following equation:

$$\frac{\text{Number of patients having tumor size decrease} \geq 30\%}{\text{Total number of the patients be monitored}} \times 100\%$$

Figure 4A:
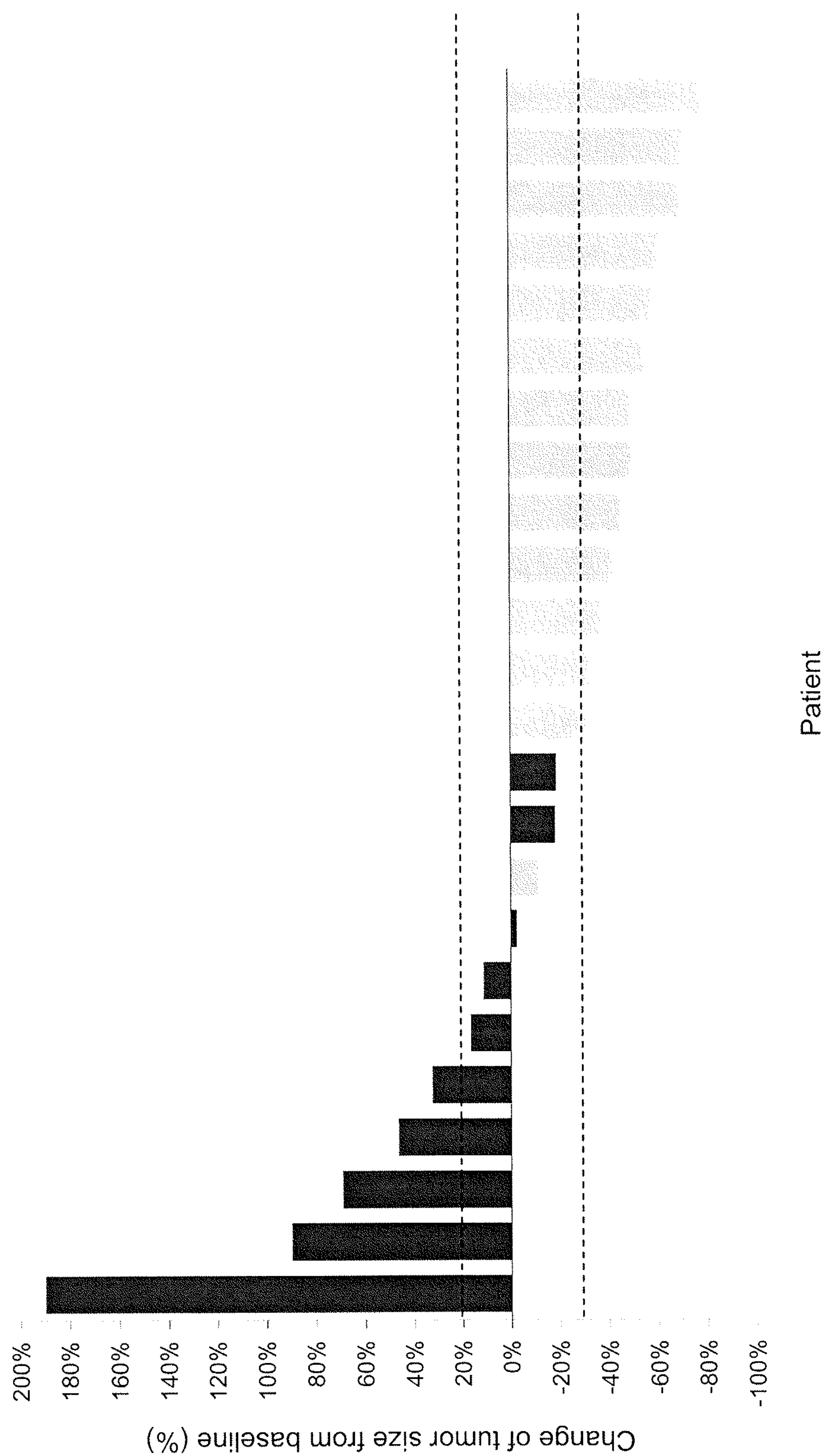
FIGS. 4A and 4B show the waterfall plots of tumor size percentage change from baseline in measurable tumors. (A) data from the 29 patients in Example 2; wherein 24 of them were monitored. (B) data from the 158 patients in Example 3; wherein 155 of them were monitored.

We evaluated individual tumor responses to EGFR-TKIs in patients whose tumors were of measurable sizes. 24 of the NGS-screened 29 patients (in above Examples 1 & 2; wherein 10 of them are with MLH1 V384D mutation and 14 of them are without) were monitored, and the tumor responses and PFS clustered correspondingly (FIG. 4A); 5 of 10 (50%) patients with short PFS had progressive disease (increase of tumor size ≥20%) whilst on EGFR-TKI treatment; and 5 of 10 (50%) patients with short PFS had stable disease (increase of tumor size ≤20% to decrease of tumor size ≤30%). 13 of 14 (92.9%) patients with long PFS had a partial response to EGFR-TKIs (decrease of tumor size ≥30%). The response rate for patient with MLH1 V384D mutation is 0%.

Figure 4B:
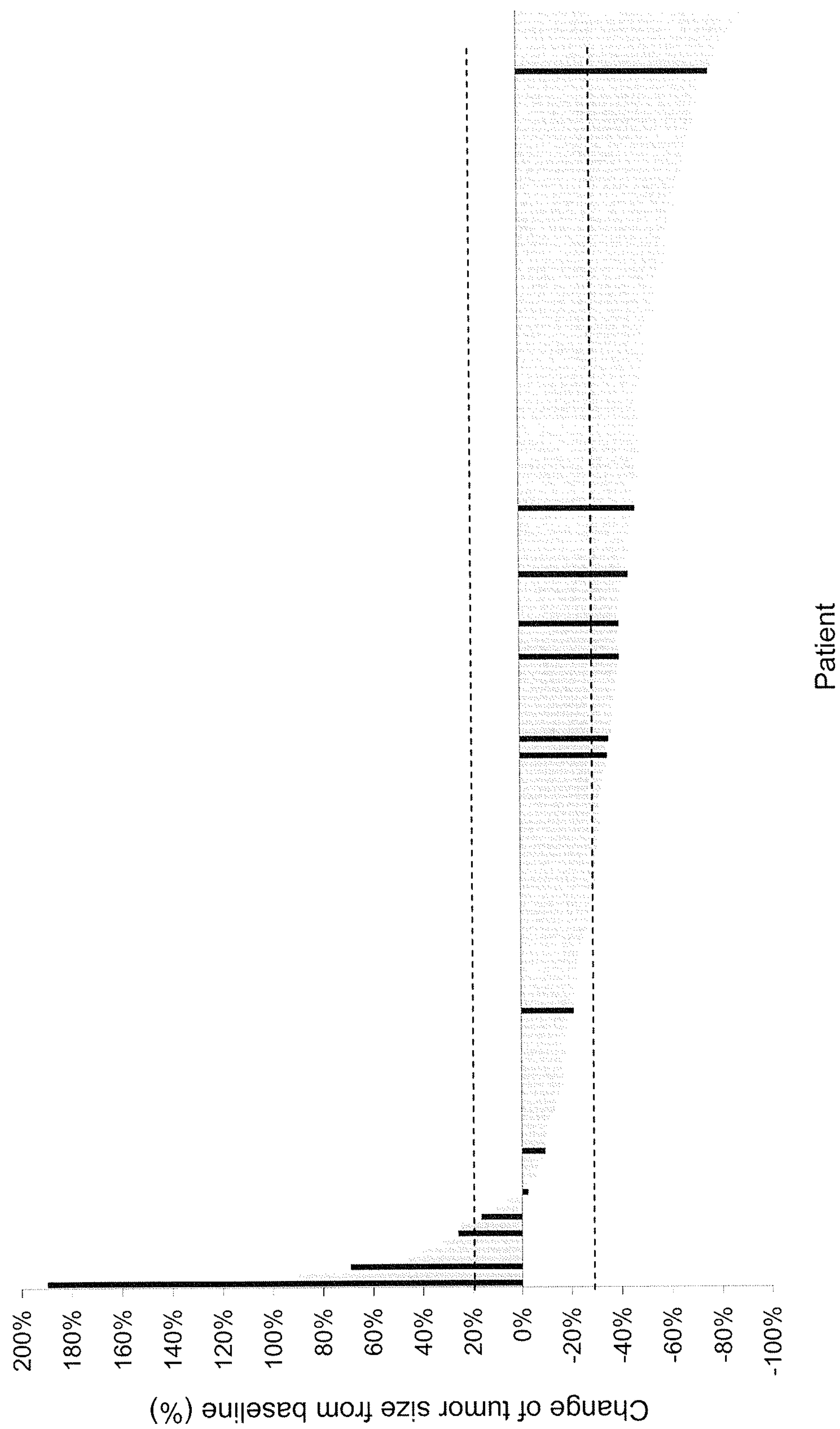

A same examination was also conducted in the 158 patients examined for MLH1 mutations by PCR and Sanger sequencing in the above Example 3. Among the 158 patients, 155 had measurable tumors and their responses to EGFR-TKIs were monitored (FIG. 4B). The overall response rate was 69.7%; 108, 39 and 8 patients achieved partial response, stable disease and progressive disease, respectively. The response rates for tumors with and without MLH1 V384D mutation were 50% and 71.6%, respectively (P=0.088). MLH1 V384D-positive tumors had a smaller size reduction in response to EGFR-TKI treatment than that in tumors without the allele (median size change −28.2% vs. −40.5%, P=0.015, Mann-Whitney U test). The MLH1 V384D allele was over-represented in patients with EGFR-TKI resistance. Only 11 of 155 (7.1%) EGFR L858R-positive tumors showed disease progression under EGFR-TKI treatment, and 4 of these 11 (36.4%) had MLH1 V384D. Among the 144 tumors either showing a partial response or being stable on treatment, only 10 (6.9%) were MLH1 V384D-positive.

Example 5: Survival Analysis

In this example, the 158 patients in the above Example 3 were monitored to record their progression-free survival (PFS). At the time of analysis, with a median follow-up of 47.4 months, 51 patients remained in use of an EGFR-TKI treatment and 107 patients (67.7%) had experienced PFS. The overall median PFS was 10.5 months (95% CI, 8.1 to 12.8 months).

Figure 5:
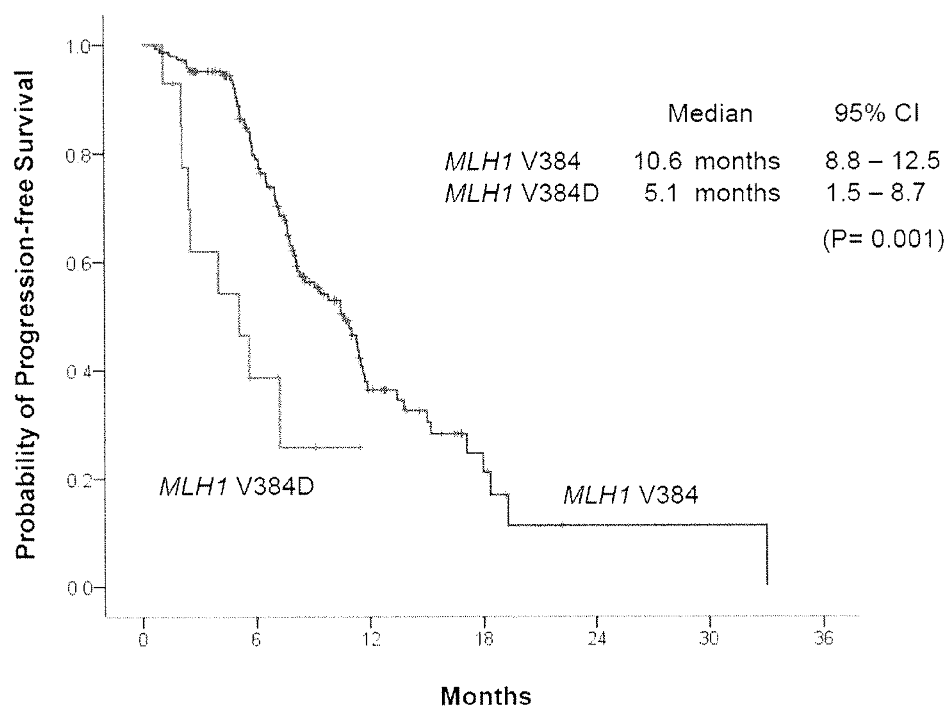
FIG. 5 shows the progression-free survival of the 158 patients of Example 3 after EGFR-TKI treatment.

Patients with the MLH1 V384D mutation had a significant shorter PFS (median, 5.1 months; 95% CI, 1.5 to 8.7 months) than that of those without (median, 10.6 months; 95% CI, 8.8 to 12.5 months) (P=0.001) (FIG. 5, Table 2). Gender (male vs. female, P=0.031) and the number of prior chemotherapy (0 vs. ≥1, P=0.002) were also predictor variables for PFS. In the multivariate analysis using the Cox regression model, only the number of prior treatment (HR=2.3, 95% CI, 1.4 to 3.8; in favor of none; P=0.001) and the MLH1 mutation status (HR=3.5, 95% CI, 1.7 to 7.2; in favor of no V384D mutation;

P=0.001) were independent predictors for PFS.

TABLE 2

Numbers of progression-free subjects after EGFR-TKI treatment

| Months | 0 | 6 | 12 | 18 | 24 | 30 | 36 |
|---|---|---|---|---|---|---|---|
| MLH1 V384 | 144 | 94 | 24 | 6 | 2 | 1 | 0 |
| MLH1 V384D | 14 | 4 | 0 | 0 | 0 | 0 | 0 |

What is claimed is:

1. A method for treating a subject with lung cancer with a non-EGFR-TKI treatment, comprising:

(A) obtaining a sample from said subject;

(B) analyzing a MLH1 protein of said sample to identify an alteration at V384 of said MLH1 protein;

(C) detecting a V384D alteration in said MLH1 protein of said sample; and (D) administering a non-EGFR-TKI treatment to said subject.

2. The method of claim 1, wherein said analyzing is performed by Western blot.

3. The method of claim 1, wherein said analyzing is performed by using an antibody.

* * * * *

SEQUENCE LISTING

```
<160> NUMBER OF SEQ ID NOS: 8

<210> SEQ ID NO 1
<211> LENGTH: 756
<212> TYPE: PRT
<213> ORGANISM: Homo sapiens

<400> SEQUENCE: 1

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
```

```
            180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
        275                 280                 285

His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
        355                 360                 365

Ser Ser Thr Ser Gly Ser Ser Asp Lys Val Tyr Ala His Gln Met Asp
    370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
        435                 440                 445

Gly Asp Thr Thr Lys Gly Thr Ser Glu Met Ser Glu Lys Arg Gly Pro
    450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
        515                 520                 525

Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605
```

```
Glu Tyr Ile Val Glu Phe Leu Lys Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755
```

<210> SEQ ID NO 2
<211> LENGTH: 57497
<212> TYPE: DNA
<213> ORGANISM: Homo sapiens

<400> SEQUENCE: 2

```
gaagagaccc agcaacccac agagttgaga aatttgactg gcattcaagc tgtccaatca     60

atagctgccg ctgaagggtg gggctggatg gcgtaagcta cagctgaagg aagaacgtga    120

gcacgaggca ctgaggtgat tggctgaagg cacttccgtt gagcatctag acgtttcctt    180

ggctcttctg gcgccaaaat gtcgttcgtg gcaggggtta ttcggcggct ggacgagaca    240

gtggtgaacc gcatcgcggc gggggaagtt atccagcggc cagctaatgc tatcaaagag    300

atgattgaga actggtacgg agggagtcga gccgggctca cttaagggct acgacttaac    360

gggccgcgtc actcaatggc gcggacacgc ctctttgccc gggcagaggc atgtacagcg    420

catgcccaca acggcggagg ccgccgggtt ccctgacgtg ccagtcaggc cttctccttt    480

tccgcagacc gtgtgtttct ttaccgctct cccccgagac cttttaaggg ttgtttggag    540

tgtaagtgga ggaatatacg tagtgttgtc ttaatggtac cgttaactaa gtaaggaagc    600

cacttaattt aaaattatgt atgcagaaca tgcgaagtta aaagatgtat aaaagcttaa    660

gatggggaga aaaacctttt ttcagagggt actgtgttac tgttttcttg cttttcattc    720

attccagaaa tcatctgttc acatccaaag gcacaattca ttttgagttt ctttcaaaac    780

aaatcgtttg tagttttagg acaggctgat gcactttggg cttgacttct gattacccta    840

ttgttaaatt agtgacccct cttagtgttt tcctgtcctt tatttcggag gacgcacttc    900

gaagatacca gattttatgg gtcatccttg gattttgaag cttataactg tgacaaaaaa    960

tgtgaaggga agagatttga aacatgtgga aggaaaagtg agtgcagact ataaacttcc   1020

aaaaagacaa gcccaaaata cacctaaacg ttatgtcaga ttattttgtt aaaatcagtt   1080

gttagtgacg tccgtacgtt aatagaaaaa agaatgcttc agtttggagt ggtaggtttc   1140

tagagggatt tattgtgaaa gtataaacta ttcagggcaa tgggactgag agaacagtgg   1200
```

-continued

```
gtagaaagga ccactgaagg aaaggaagag aattggaagg tagatgaaag aaggagcaag   1260
aacctgggga tgtttttcc ttttcacttg taatagtagt aacagaagca atggcagact   1320
ggcttttgtt tctactgtgt tagaatgaat tgacaggaca actgggccta ttattgtact   1380
gtgccagaat actgtaaaac aaaactaaac atactagctt ggtggcttgt aattaattac   1440
ttaagtggag atttttattt tttttttatt tttttttag acggagtctc actttgtcac   1500
ccaggctgga gtgcagtggc gcgatctcag ctgactgcaa cctcctcctc acaggttcaa   1560
gggagattct cctgcctcag cctcccgagt agctaggact ataggcatgt gccaccacac   1620
ctggctaatt ttgtattttt agtagagatg ggatttctcc atgttggtca ggctggtgtc   1680
aaaactctcg atctcaggtg aaccgcctgc ctcagccttc caaagtgctg ggattacagg   1740
cgtgagccac cgcgccctgc agttttttgt atttttaata gagacagggt ttcaccatgt   1800
tagccaggat ggtctcgatt tcctgacctc aggtgatctg cccgctttgg cctcccaaag   1860
tgctgggatt acaagcatga gccaccgcgc ccggctcaag tggagatttt tatatggagt   1920
ccagttatac tctttttaat atataagttg agatgactaa tacaacttca atacaggggc   1980
tcatgagaaa tgtctgtaat atttaagtaa cttattgtct tctttctttt ttttttaaga   2040
tgaagtctta ctctgttgcc caggcggaag tgcagtggcg tgatcttggc tcagggcaac   2100
ctctgcctcc tggtttcaag cgatcttcct gcctcagcct cccgagtagc tgggagtaca   2160
ggcgtgcatg accacacccg gctaattttt ttatttttag tagagacggg gtttctccat   2220
gttggccggg ctggtcttga actcctgacc tcaggtgatc cgcccacctc agcctcccca   2280
agtgttggga ttacaggtgt gagccccccgt gcccagccta ttatcttatt tctgaataaa   2340
gaattgtctg tgtggggaat agataactct ttctcatgca gcccctgcta gaaaatttgt   2400
tttctctagc agttggtctg tgcttatagg ctactctttg aaagcacaaa aaatttattg   2460
acttcttttt tttgggtttt tttttttttt tgagacagag ttttgccctt gttgcccagg   2520
ttggagtgca atggcgcgat ctcagctcac cgcaacctcc acctcctggg ttcaagtgat   2580
tctcctgcct tagcctcctg agtagctggg attacaggca tgcgtcacca tgcctggcta   2640
attttgtatt tttagtacaa atggggtttc tccatgttgg tcaggctggt ctcaaactcc   2700
tgacctcagg tgatccaccc gccttggcct cccaaagtgc tgggattatg ggtgtgagcc   2760
attgcgcctg gccagaaaat tcattgactt cctaaagatt tattaacttt ctgcattact   2820
ttttttttc ccctccatcg taaatataaa agggaatagt agagaaaatc attcagaatt   2880
ttattttta gtgacattat ttagtgacat tttattagag tcacttagga acctgaggct   2940
gaataaagtt caggtaaaag taaaattagt tgagaagaga catctgccaa aagaaatcta   3000
tttttaactt cacttgctgt ctttcctaga ggaacagaaa tagtgctgaa tgtcctatta   3060
gaaatgatgg ttgctctgcc cgtctcttcc ctctctctca cacaatatgt aaactcatac   3120
agtgtatgag cctgtaagac aaaggaaaaa cacgttaatg aggcactatt gtttgtattt   3180
ggagtttgtt atcattgctt ggctcatatt aaaatatgta cattagagta gttgcagact   3240
gataaattat tttctgtttg atttgccagt ttagatgcaa aatccacaag tattcaagtg   3300
attgttaaag agggaggcct gaagttgatt cagatccaag acaatggcac cgggatcagg   3360
gtaagtaaaa cctcaaagta gcaggatgtt tgtgcgcttc atggaagagt caggaccttt   3420
ctctgttctg gaaactaggc ttttgcagat gggatttttt cactgaaaaa ttcaacacca   3480
acaataaata tttattgagt acctattatt tgctgggcac tgttcagggg atgtgtcagt   3540
gaataaaata gattaaaatc tattctcttc tgatgcttac attatagtgg tgggagacaa   3600
```

-continued

```
aatgggtata ataaatatta tattagatag cattaagtgc tgtggagaaa actaaagcag   3660
ggaggaagat aggagtgtgc aagccagaaa ggttgcaatt aaattgagta gttcaggaag   3720
gcttcaatat ggatgtgata tttgagagac cggtggaagt caaggagcaa gttgtgaggc   3780
tatttaaagg tattcttggc ttacagaaca atatacgcaa agactattaa atggaagcat   3840
acctgacatg ttaaaggact atcaaggagg ccagtttgtc tagaggctga aaaggaaaga   3900
gtaataggag atgaggtctg agtgaaaaca cgtaaatcct tgtgggccaa ggtaaaatct   3960
ttagcttttt ttctgaatat ggtgggatac tgttagaggg ttttaagcag aggttacgtg   4020
gtgtggtgag tttttttttt ttaatccttt gtctttctgt gtggaaaata gcaggacagg   4080
gcagaagcag tctgtcctgc agactgcttg gtcgcagtag agatgtaaga agcagtgaga   4140
ttctgggtta attatggagg caaagttctc agaatttgct gatatagggt atgagagaaa   4200
gaggaatcag gaatgatttc aaggttttgg tctgctaaat ggaaggagtt gccatttact   4260
aagatgggaa agactatgaa agaagcagat tttcagagag atcagaagtt cattttgggg   4320
catgttcaat ttaagatgcc tgttagttgg atgtttatgt gagtttggaa tgcagggtag   4380
agatttaggg atgaatattt ggtagttgtc tgcattttaa tggtattaaa agccacgaga   4440
aggatgggca tggtggctca cacctgtaat cccagcactt tgggaggcca aggcgggcag   4500
atcacctgag gtcgggagtt cgagaccagc ctgaccaaca tggagaaacc ccatctctac   4560
taaaaatata taattagccg ggcgtggtgg cacatgcctg taatcccagc tactcgggag   4620
gctgaggcag gagaatcgct tgaacctggg aggtggaggt tgcgatgagc cgagatcgca   4680
ccgttgcact ccagcttggg caacaagagc aaaactccat caaaaaaaaa aaaaaaaaaa   4740
aaaaaaagcc ttgagactca cctgaaaaga tgctcaacat tattggtcat taggaaaatg   4800
aatgaaaacc acaatgagat accacttcac acctattagg atggctatta tcaaaaacaa   4860
aaacaagtgt ttgcaaggat gtagagattg gaattcttgt gtattgctag agggaatgta   4920
aaatagtgca gggtgctgtg gaaaatgctg tggtgattcc tcaaaaaatt aaacataatt   4980
atataatcca gtaattccac ttctgagtta ttcccaaaag aagggatgca agcagatatt   5040
tgtacactca tattcatggc agcattattt acagtagcca aaaggtgaaa gcaacctaag   5100
tgtccgtcag tggatgaatg gataaacaaa atggaataat ttcagcctta aatagaaata   5160
aaatgttgac acatgttgca acatatacga accttgaaga catcatgtta agttaaataa   5220
gttggtcact aaaggacaaa tattgtatga ttccccttat gaggttccta gagtagtcac   5280
attcatagag acagtagagt ggtggttgcc cagggccggg gggagcgagg agaatggaaa   5340
ttattgttta ttgggtacag agtttctgtt tggggaagat gaaaaaattc tggagatgga   5400
tcatgatgat agttaacaca gcagtgtgaa tatagttaat ggcacagaac tgtacattta   5460
aaaatggtta agatggaaaa ttttctgtta catatatttt actgcaattt ttttaaattt   5520
tattattata ctttaagttt tagggtacat gtgcacaaca tgcaggtttg ttacatatgt   5580
atacatgtgc catgttggtg tgctgcaccc attaagtcat catttagcat taggtatatc   5640
tcctaatgct atccctcccc cctcccccac cccacaacag tccccagtgt gtgatgttcc   5700
cctttctgtg tccatgtgtt ctcattgttc aattcccacc tatgagtgag cacatgcagt   5760
gtttggtttt ttgtccttgt gatagtttgc tgagaatgat ggtttccagc ttcatccatg   5820
tccctgcaaa ggacatgaac tcatcatttt ttgtggctgc atagtattcc atggtgtata   5880
tgtgccacct tttcttaatc cagtctatca ttgttggaca tttgggttgg ttccaagtct   5940
```

-continued

```
ttgctgttgc gaatagtgct gcagtaaaca tacgtgtgca tgtgtcttta tagcagcatg   6000
atttataatc ctttgggtat atacccagta atgggatggc tgggtcaaat ggtatttcta   6060
gttctagatc cctgaggaat tgccacactg acttccacaa tggttgaact agtttacagt   6120
cccaccaaca gtgtaaaagt gttcctattt ctccacatcc tctccagcac ctgttgtttc   6180
ctgacttttt aagatcgcca ttctaactgg tgtgagatgg tatctcattg tggttttgat   6240
ttgcatttct ctgatggcca gtgatgatga gcatttcttc atgtgttttt tggctgcata   6300
aatgtcttct ttcgagaagt gtctgttcat atccttcact cactttttga tggggttgtt   6360
tgtttttttc ttgtaaattt gagttcattg aaaaattaga attttttttt ttttcccttt   6420
tttagaggca aggtctcact ctgtcgccca cactggagtg cagtagtgta agcatagctc   6480
actgtaacct tgaactcctg ggctcaagca attctgtcat ctcagccagc tgaagtagta   6540
actgtaggtt cacaccacca tgcctatttt tgtttttgta gaaatagggc cttgctttgt   6600
tgccaaggct ggtcttgaac tcctgacctc aagcagtcct cctgtctcag cctcccaaag   6660
tgctgggatt ataggtgtga gccactgcac ccagccttgg agatttttaa taaagaagct   6720
tgtcaattaa acaaacaaca aaaagccctg agactgaatg agataatcaa gagagtatgt   6780
gtagatagag aagaggtcca aggaaggagt cttgggtgac tctgatgtca agtgaggaca   6840
tgaggcagaa acagcagtga ctgagaagga gccacctagt aagaaaggag gaacaccagg   6900
acagtgtggt attctggatt ccaaacaagg aagttactgc taattttaaa gctcttctca   6960
ggctgggcat ggtggctcac acctgtagtc ccagcacttc gggaggctga ggtaggtaaa   7020
tcacttgagc tcatgtgttt gagaccagct tgggcaacat ggtgaaacct catctctact   7080
aaaaatataa gaaattaagg ccaggtgtgg tagttcatgc ctgtaatccc agtgctttgg   7140
gaggtcaagg cagccagatc atttgagatc aggagttcga gaccagcatg gccagcatag   7200
tgaagcccca tctctactaa aaatacaaga aaaaattaac caagcatggt ggcgcatacc   7260
tgtaatccca gccactctgg aggctgagac atgaaaattg cttgaacccg ggaggcggag   7320
gttgcagtga gctgagatct cgccactgca cttcagcctg ggtgacagag caagactctg   7380
tctcaaagga ggttgcagtg agctgagatc tcgccactgc acttcagcct gggtgacaga   7440
gcaagactct gtctcaaaaa aaaaaaaaac aaaaaccaag aaaagaaaaa aaaactcttc   7500
taagaggatt tttttttcct ggattaaatc aagaaaatgg gaattcaaag agatttggaa   7560
aaatgagtaa catgattatt tactcatctt tttggtatct aacagaaaga agatctggat   7620
attgtatgtg aaaggttcac tactagtaaa ctgcagtcct ttgaggattt agccagtatt   7680
tctacctatg gctttcgagg tgaggtaagc taaagattca agaaatgtgt aaaatatcct   7740
cctgtgatga cattgtctgt catttgttag tatgtatttc tcaacataga taaataaggt   7800
ttggtacctt ttacttgtta aatgtatgca aatctgagca aacttaatga actttaactt   7860
tcaaagactg agaattgttc ataaataaac tattttacct gcagagacct ctgatatatg   7920
tttcttgatg gaagtaccca gtaccaccta tgaagttttc ttgtcaaaaa atcaaatgtg   7980
aatctgatca ttacttagat ctaagtacca atatatgaaa aatataggag acaaggaagc   8040
atggtaaatg atactgagat tgggagacta catggaaaaa gacttgttcc cttcaacaga   8100
tagacagcag ggaaaaaaga atagagaaag gagtaaagaa cctgtagatt aaaagacatt   8160
taagggacat atgaaccagg tccagtgtat agatcttacc taaatcctga tggagcaaac   8220
tataaaaaaa tttttttgag acaaatgttt gaatacaggt tgactatttg atggcattaa   8280
ggagaaatta tgaattatct tggtataaga atattgtcat gggttttttt ttttgagtcc   8340
```

```
ttacctgtta agatacatac taaaatattt gtgggtaaaa ttatatgacg tataggagta   8400
tatgatttag aaaacggatt aaaatataaa aggataaaat aggatcttat attttgtgac   8460
tcacttcctg ttggatatct ttctacccag taaatatagt cctatctagg ttttaatggc   8520
tacatgtatg tactgtagtt tgtttaaatg gtttcctatt gaacatttat gctctttgcc   8580
attttttcct gtttaacgtt ctgttttttt ttttgttttt tttttttttt gagacagtct   8640
tgctctgtta tccagactgg agtgcagtga catgatctca gctcactgca acctctgcct   8700
tctgggttca agctattctc ctgcctcagc ctcctgaata gctgtgatta caggcgtgca   8760
ccactatgcc cagctaattt ttgtattttg ggtagagaca gggtttggcc atgttggcca   8820
ggctggtctt gaactcctga ccttgaatga tctgcccgcc ttggccttgc aaagtgctgg   8880
ggttacaggc atgagccacc acgtctggcc ttgtttaagg tcctgatgag tattcttata   8940
ggtacactgt gtttcgttta attatttcct taggataaat ttatagaaat aacattcctt   9000
ggtaaaagaa tacatatttt aaaaactgta ttagtttcct gttgctgtca aaaaatttcc   9060
agaaacttag tggcattaaa caatacaaat taattattct acagttctgg agatcagaag   9120
atacgggtct tactaggcct cactaggcta aaatcaaggt tttggcaggg ctgtgttcct   9180
ctatggaggt tccaagggac cagagaaact actttacagt agttatttta agggaatgaa   9240
agtgaagatg gggttgggca gtcaaagagg ctgttacttt tcatttttgg cctttcagta   9300
gtttgaattt ttttatcata tacatgtatt actttaattt ttaaaaagta aaaagcagct   9360
gtgattcagt ctctgtaatt tagatcaatt tacatcaaac tagggtggtc tcatgtgttg   9420
tcttgctcac agtgaccact agattattcc aagaagggac aatttccaag acttggttta   9480
cactgagacg gctcctgatt ttaaggatac cttagatcaa actctaggaa ggcagtttca   9540
ttttggcctt gcagttccct gggtcatttt ccaagcccat ggcctcctgg agtcttcgcc   9600
tagctgtagg ttatctttgt ggctattatt tcactgtaat tatacaggaa gatttattga   9660
gggatttctg tgtaccagcc gtggttctca gcactttgta tactttgtat taactctgac   9720
tcctgacagt aactctacag aggttctgct gttacccagt tttacataga aacatggcca   9780
gcggacgcag ttagaaaatg gcaaagtggg gattagaaac taggcagttt gactccagag   9840
tctgtgcccc tgtccacttg gctccactgc tggggaagag gcctctgaag cagcaggacc   9900
atctgctgtg ccgtgtgtag tggtactcta tcttcctggt gtgatgttgt gttctacttt   9960
gcattttcat gtctttcctt atacaggtct caaaatcatt tacttttttt tttttttttt  10020
tgagacggag tctcactctg ttgcccaggc tagagtgtag tggcatagtc tcactcactg  10080
caacctccgc ctccgaggtt caagtaattc tcctgcctca gcctcccaag tagctcggat  10140
tacaggcaca tgccaccaca gctagcaaat ttttgtattt ttagtagaga ttggtgtttc  10200
accatgttgg ccaggctgtt cttgaactcc tgacctcagg tgatccaccc acctaggcct  10260
cccaaagtgc tgggattaca ggcgtgagcc accccaccca gccttatatt ttttaatgat  10320
gcacattagc tcaattacat aaaccaggga aatccagcta ggacctggtg atttctgagc  10380
ctgacccatg tgactttcaa tgaactgaac ttgccacagc tgtatttact gtctactgag  10440
atgctgtcac acagaccccg tcatagcaca gttcctgagt tacatcttta catactgtag  10500
tatccttctt gtgaaaaaag atacagattc caaaggtctg agaaaccaat cttggttata  10560
aaggggaaaa atggtcatgg gtttttaaaa tttgttttgt cttaattgca tttcaaattt  10620
acatttctaa atgaataatt gcttatataa agcagttttg attaacaata taaaacacta  10680
```

```
tctatttgga gtgattcctt tacccatttc tgaaggcaag ttttaaaaat tactagaaga  10740
cacttcattg agaatattat taaacatgcc tatagttcta ccacctcaac acaattgctt  10800
attaacacat taatgttttg gtgtgttttg gactttttaa tatgtatttt tcacttgttc  10860
tagtaattat gctacagatt gatcatttct ttttcaacat gtcatcaaag caagtgagca  10920
aagtgctcat cgttgccaca tattaataca aaatggaagc agcagttcag ataacctttc  10980
cctttggtga ggtgacagtg ggtgacccag cagtgagttt ttctttcagt ctattttctt  11040
ttcttcctta ggctttggcc agcataagcc atgtggctca tgttactatt acaacgaaaa  11100
cagctgatgg aaagtgtgca tacaggtata gtgctgactt cttttactca tatatattca  11160
ttctgaaatg tattttttgc ctaggtctca gagtaatcct gtctcaacac cagtgttatc  11220
ttttttggca gagatcttga gtacgttttc ttttctcctt attgataaat tgataatcct  11280
caaggatgat tattaggtga tactcttact tcatggattc ttaaaagata tgatttaaca  11340
tattacaagt gcctagcaag gtgtctgtta cacgtaggta ttttaagtaa atggtagctg  11400
ctgatgtaat ttctgcccct ttgcccttca gttggggtat tgctttggac cgattagagg  11460
gctgtggctg ggatgctaaa ggttcatgtt tccttagctg gctcctgagc caccagctcc  11520
caccacctgt gtatacctgt gctagtttgc cttcccacaa gtagctgctg gctatctgtt  11580
atgctggtac agttttcaga aactgatgaa tggcctttga acagaacaaa aatgagattc  11640
agaataacaa aattgcacct ttgtttttat aagcactggc cattcactag ttgaagactg  11700
gtaggaatac ctaattcatg ccaaaagaaa gataattttt aaaaatcaca caggttgttt  11760
gtagattaaa agggaaaata ggctaggtat agtggctttg cctgtgagtt tgggaggctg  11820
aagtgggagg attgcttgaa gtcaggagtt tgagaccagc ctgggaaaca gagcaagacc  11880
ccgtctctac agaaaatttt taaaaaatta gctgggcatg gtgatgcata tctgtagtct  11940
tagctactcc ggaggtggga agattgcttg agcccagcag tttgaggctg cagtgagctg  12000
tgattacacc actgtactcc aaccttaaaa taaataaata aataagggaa aatatcttca  12060
acaaaggata gttctgtctg tttctcagtc ttcctcaaca gataaatgtg tgaagtaatg  12120
gaaggtggag atttcagatt acacaacatt aatgctaagg gcgtttgact ctgtgtgaat  12180
tctaattgcc ctagatctag acgggctgat actattagaa tcccctgtca ctaactgaag  12240
acagagttgt aagttaatgc cttcctagat agcctagatt gtggtatgct gctgcatgct  12300
aaaatggctc cccttccata gcaggatgaa atagagtcat tatcttggca accagcccct  12360
gccaatgtgc tctcagtctg cctttccagc cccttctctc tacctattcc cagctgccat  12420
gtattctaaa gcctctatgc tttcattttt gtttttgcct tcctggatgg tctttcctgc  12480
tgtctccacc tgaaactatt cctctctaaa gaacagatga attgccatct ctctgggatg  12540
cttttaccca ccctcactcc cacctcaggc tgaatggacc cttctctaga tcgcttagca  12600
tattgttcta cagttaggta aaaagtctac ctatcactag atcaagagct ttgttttttt  12660
ttattaattt aattttcttt tttttttttc tttttttttt gagacagagt ctcgctctgt  12720
cgcccaggct ggagtgcagt gcacaatctt ggctcactgc aagctccgcc tcccaggttc  12780
acaccattct cctgcctcag cctcccgagt agccgggact acaggcgccc accaccacgc  12840
ccagctaatt ttttgtattt ttagtagaga cggggtttca ccatgttagt tagccaggat  12900
ggtctcgatc tcctgacctc gtgatccacc cacctcggcc tcccaaagca ctgggattac  12960
aggcatgagc caccgcgccg agccccaaga cctttcttta ttaccagggc ttccacagac  13020
ctgacacatg gtagttcctc aataaataat tgcagaatta ctgaaaaatt ttactgttaa  13080
```

```
cttaggcagt ggtaaaacca ttgtttggta gctcagaact cagcaagtaa atagcaacat  13140
ttgctggaag aacagatagt ttttcaaatc caattcaagg actgggtatg gtggctcatg  13200
cctgtaatcc cagcactttg ggaggccgag gcaggcgtat ccaggagttc gagactagcc  13260
tgaccaacat ggtgaaactc cgtctctact aaaaatacaa aattagccag gtgtggtggt  13320
gggcacctgt aatctcagct acttgggagg ctgaggcagg agaatcgctt gaacctggta  13380
ggcggaggtt gtagtgagct gagattgtgc cattgctctc cagcctggga aacaagagca  13440
aaactccgtc tcaaaaaaaa aaaaaatcca attcaaatga ttatggaagt agtggagaaa  13500
taaacaggaa aatgataaat aattaagata atatataata tggctatatt ttaatctatt  13560
gttgatatga ttttctcttt tccccttggg attagtatct atctctctac tggatattaa  13620
tttgttatat tttctcatta gagcaagtta ctcagatgga aaactgaaag cccctcctaa  13680
accatgtgct ggcaatcaag ggacccagat cacggtaaga atggtacatg ggagagtaaa  13740
ttgttgaagc tttgtttgta taaatattgg aataaaaaat aaaattgctt ctaagttttc  13800
agggtaataa taaaatgaat ttgcactagt taatggaggt cccaagatat cctctaagca  13860
agataaatga ctattggctt ttgtggcatg gcagcctgcc acgtccttgt ctttttttaag  13920
ggctaggaga ttctttattg ggatggcaaa agtcaatggc agggtagttg tcattgaaag  13980
aagattaagc ttgaccccag aaggcatggg ttagagccca gccttgtcac tcaatggttg  14040
tatgtccaga ggcaagtcac ttaacatccc ttaaccccag ttttctcatc tgtcaaatga  14100
agcaaagaat acttgccctc ttgacttaaa gggtgtctga tgagacatat gactgtatca  14160
ttagctggga gaaagtccat cgtgctgcct atgtatagtg cctcaagttg gtctctttcc  14220
cttctatgat tacacaaagc actccgctgt catgttatcc atcccgcccc tccattccaa  14280
gtcccatcta gagcacatct tcttgaagtc cactgtaacc tgcctaatcc tggatgtgac  14340
gagccaggca ggaggcagaa aagaatgtgt gttttgcaat acatgttaag agacatcttg  14400
ggctgggcac ggtggctcac acctgtaatc tcagcacttt gggaggctga ggagggcgga  14460
tcatctgagg ttgggagttc gagaccagcc tgaccaacat ggagaaaccc catctctact  14520
aaaaatacaa aattagccag gcgtgatggc gcatgcctgt aatcccagct actcaggaag  14580
gctgaggcag gagaattgct tgaacccggg aggcagaggt tgtggtgagt tgagatcatg  14640
ccactgcact ccagcctggg caacaagagt gaaacagggt ctcaaaaaca aaaacaaaca  14700
aacaaaaaaa atcttttacc acggtgacca ccatgtgatt tccaagaact tcaaatgatc  14760
taagaaattt tgtgattatt actagtttga aaaatacttt tttttttttt gagacaaagt  14820
ctcactctgt tgcccaggct gaagtgcagt ggtgtgatct cagctcactg caatcactac  14880
ctcttgagtt caagcagttg tcctgcctca gcctcttgag tacctgggat tacaggcatg  14940
cgtcaccatg cccggctaat ttttgtattt ttagtagaga cagggtttca ccatgttggc  15000
caggctggtc tcgaactcct gacctcaggt gacccaccca ccttggcctc ccaaagttct  15060
gggattacag acgtgagcca ctgcacccag cctgaaaaat atctttgaat gccatgtgat  15120
actatacttg tcagtttaca tgtgtgtccc actaaatcat gtactctcct gagcaggatc  15180
atgctttgtc ttcatatttt ctgtacaaag caaagactct gacacaaagc tagcccccag  15240
tgcatagttg agaaatcagt gaatgaatgt gggaggcagg aaaaatgtcc tttaattctt  15300
ctgttaatgc tgtcttatcc ctggccccag tcagtgctta gaactgtgct gttggtaaat  15360
ataattggat tcactatctt aagacctcgc ttttgccagg acatcttggg ttttattttc  15420
```

```
aagtacttct atgaatttac aagaaaaatc aatcttctgt tcaggtggag gacctttttt  15480
acaacatagc cacgaggaga aaagctttaa aaaatccaag tgaagaatat gggaaaattt  15540
tggaagttgt tggcaggtac agtccaaaat ctgggagtgg gtctctgaga tttgtcatca  15600
aagtaatgtg ttctagtgct catacattga acagttgctg agctagatgg tgaaaagtaa  15660
aactagctta cagatagttt ctggtcaagg tttagccacc aattttgcag tttctctcat  15720
ctccccagga aagagcagtt ggtctttaga tcaatgagag ctcttttatg gcagacaaaa  15780
caaagtgact ctagccaact tgagctaaaa agaaatttag tggaaggcta ggagttacca  15840
catgaagtgt gtgcagctgc cccttggaga gaataagaac cagggtgcct ctgggactta  15900
acatcattac tgtactccag ttgttttcat tcttttcctg actttgctct agagtcagtt  15960
tcctaacaga gtacattcga tgatcatgtg cccatatctg tggggagaag atttcttgat  16020
tggcagtctt actaagggtg catatcaagt agaatggaat agaggtagtt tcctaaagga  16080
agatgagagg ctgttaccag gaggaggaga agggattcag gacagatgaa aacaacgtta  16140
tatccatgat agacttacgc tgctggtaca gatggtacag gtggcttcag tataggctct  16200
ccgaacccac atatcattga ttatgatagg gatatgttaa ctatttttca gtgtatatat  16260
gtatatgtgt gtgtgtatat atatgtatat gtatatatat atgtatgtgt atatatgtat  16320
atgtatatat ttatatatgt atatgtatat atttatatat gtatatgtat atatttatat  16380
atgtatatgt atatatattt atatatgtat atgtgtgtat atatatattt atatatatgt  16440
atatgtgtgt atatatatat attttttttt gaaacggaat ttcgctcttg ttgcccaggc  16500
tggagtgcaa tggtgcgatc tcagctcact gcaacctctg cctcctgggt tcaagcgatt  16560
ctcctgtctc agcctcccga gtagctggga ttacaggcac ttgccaccat gcccggcaat  16620
tttttttttg ttttttttta gtagagaggg ggtttaatca ttttggccag gctggtcttg  16680
aactcctgac ctcaggtgat ctgcctgcct tggcctccta aagtgctggg attacaggcg  16740
tgagccacca tgcctggcca tttttcagta tttctttttt tttttttttt tttttttttt  16800
ttgagacaga gtttcactct tgttgcacag gctggagtac aatggtgtga tctcggctca  16860
ccgcaacctc tacttcccag gttcaagcaa ttcgcctgcc tcagccttct caagtagctg  16920
ggattacagg catatgccac catgcccggc taattttgtg tttttagtag agatggggtt  16980
tctccatgtt ggtcaggcta gtctcaaact cccgacctca gatgatcctc ccgccttggc  17040
ctcccagagt gctgggatta ctggcatgag ccagcgctcc tggcccattt ttcagtattt  17100
ctaaaaaaaa tctaaagtgg gtcaaacatt tcaccttaat agaatgacag gtttgtacat  17160
caagtttctt tgctttttct tggaatttta tacttttttt ttttttttgg agacagagtc  17220
ttgctgtgtt acccaggctg gagtgcagtg gtgcgatctc agctcaccac aacctccacc  17280
tccaggttga agcaattctc ctacctcagc ctcctgagta gctgggatta caggcacatg  17340
ccaccacacc cggctaattt tttttttttt tttgtatttt tagtagagac agggtttcac  17400
catgttgtcc aggctggtct cgaactcctg acctcaggtg atccgcccat ctcggcccac  17460
caaagtgctg ggattacagg cgtgagccac tgcacccggc ctttttcttg gaattttatc  17520
aatcagtgtc agaatattca ttacctccta aaaataaagg agttctagtt ggctgttttg  17580
attctaggtg tggtaaagtg aaatattgtt acttaataaa tgcattttgc tagacacaat  17640
ccttcggttc acgagctctg tagagaaaag agaaataacc gccaaccaag aaaagattgg  17700
gagatactag aataagaccc aggggcagga agaagccagt gagaaggagg gcatgttgag  17760
agctctgaga gagaataaaa gcaggggttg ttggagctag cttctcaaga tgtccttgag  17820
```

gcaaaccaga cctttgggac actctgaaaa taaaactgaa agtgaagaga ttgtgggccg 17880
aatgtggtgg ctcacgcctg taatcccagc actttgggag gtcgaggcgg gtggatcacc 17940
tgagatcagg agttcgatac cagcctggcc aacatggcga aacgccatct ctactaaaaa 18000
tacaaaaaaa attagctggg cctggtggca ggcgcctata atcccagcta ctcgggaggc 18060
tgaggcggga gaatcgcttg agtccaggag gcggaggttg cagtgagctg agatcgtgcc 18120
attgcactcc agcctgggca acaagagcaa aactctgtct caaaaataaa taaaaataaa 18180
taaaaaagag atagtggcgt gatatccttg attctatcag caacctataa aagtagagag 18240
gagtctgtgt tttgattcag tcacctttag catttttatt tccatgaagt ttctgctggt 18300
ttatttttct gtgggtaaaa tattaatagg ctgtatggag atatttttct ttatatgtac 18360
ctttgtttag attactcaac tccactaatt tatttaacta aaagggggct ctgacatcta 18420
gtgtgtgttt ttggcaactc ttttcttact cttttgtttt tcttttccag gtattcagta 18480
cacaatgcag gcattagttt ctcagttaaa aaagtaagtt cttggtttat gggggatggt 18540
tttgttttat gaaaagaaaa aaggggattt ttaatagttt gctggtggag ataaggttat 18600
gatgtttcag tctcagccat gagacaataa atccttgtgt cttctgctgt ttgtttatca 18660
gcaaggagag acagtagctg atgttaggac actacccaat gcctcaaccg tggacaatat 18720
tcgctccatc tttggaaatg ctgttagtcg gtatgtcgat aacctatata aaaaaatctt 18780
ttacatttat tatcttggtt tatcattcca tcacattatt ttggaacctt tcaagatatt 18840
atgtgtgtta agagtttgct ttagtcaaat acacaggctt gttttatgct tcagatttgt 18900
taatggagtt cttatttcac gtaatcaaca ctttctaggt gtatgtaatc tcctagattc 18960
tgtggcgtga atcatgtgtt ctttcaaggt cttagtcttg aaaatattta tagtgtagta 19020
gaactatttt atcctccaat gctccttctt ttccttgtat ttccattatc atcactttag 19080
gatttcactt atttatcatt caacatttat taattgcctc tcatattcca ggctttgtgc 19140
tagaagttag ggatataaag acaaataaga tatttcctgc ccttaaagac tagattcgtg 19200
ttgctaagtc ttcattatca agaaaagcat aagtggggaa aagtgcttgc attatggatt 19260
cctcatagtt gctcccctct gcatgtaaaa atcaccattt ccatcataga ttcctagcgg 19320
tctcaggact ttataaagcc caaagtgcct atgtcataat atgaggaaaa atactgagac 19380
ccttccatat atgggaggta tatggatgag acagctcctg acttcacttt tcccagaaat 19440
ctgaaaagca gcagcagtca ttccagagcc cagtttctac tttgaagggc agattattta 19500
ttctttgagc taacctgact gaggaacaat tagtttgctt ttaatttact attttctttt 19560
tcttttcttt tctttttga gacagagtct cactctgttg cctaggctgg agtgcagtgg 19620
ctcaaacttg gctcactgca agctccgcct cccgggttca cgccattctc ctgcctcagc 19680
ctcccgagta gctgggacta caggcgcctg tcaccacacc cagctaattt tttgtatttt 19740
ttagtagaga cggggtttca tcgtgttagc caggatgatc tcgatctcca gacctcgtga 19800
tccacccacc tcggcctccc aaagtgctgg gattacaggc gtgagccacc gtgcccagcc 19860
actattttct ttctaattgt taatgaatta attttttaaa actgtgctcc tagagcgaag 19920
ggagagctct gtttacagtg taacttttca gagcttcttt aactagattt taagatcaga 19980
attagttgtt gtgaaatctt agggactgta caagattaga aatcctctat agcagcattt 20040
cccaaagcag gcttccagaa cactagcctc atgaggcatt ttgggaaaaa agagtttgct 20100
ggttcagtgt gtatgggcag tgccacaagc cgtaccctcc gttgaagaca ctcattccac 20160

-continued

```
acattactgc ataaaaagct tccaccagcc attcggcaaa cttattgagt gtctgctatt  20220
tcctgggtat tgtgctatat ggtagggtta tagtagtgaa caaagaagaa atgatgcctg  20280
ctctcagctg actttgcagt tggaaagaca catgaaataa ttacgccatt cattagcaga  20340
ttgtgctaga tgcctcactg gaaaaataaa ggacatgatg gaaaactctg tagggtcaga  20400
gaaagggatc attagagaag gttctttgaa gaaatatttt ttgaaatatg aaggataaat  20460
aggaattaac taggtaccaa taggttagga gtagagcttt ccagacagag ggactagttc  20520
ttgggaaggt ctccagacag aaataagtgt ggcttgtctg aggacctctt attcgcctat  20580
taaccttccc tccccagtaa acactcctgg gaacaacaca cattgtagaa ccacgttgtg  20640
gtgctgttca gtatagcaag taattcagca gagataagtt cttggaatct catctttggg  20700
atttagttac taagatacat tcaagtttga gcaaaataag gtctcagagc ttggattcat  20760
tgttctgttc cagcaattag agcagtacct ggcacatagc acaagtgctt gaaaacactg  20820
actgagtagg gtaggtgggt gagtgggtgg gtgggtgggt gggtggatgg atggatggga  20880
ggatgggtgg gtgaatgggt gaacagacaa atggatggat gaatggacag gcacaggagg  20940
acctcaaatg gaccaagtct tcggggccct catttcacaa agttagttta tgggaaggaa  21000
ccttgtgttt ttaaattctg attcttttgt aatgtttgag ttttgagtat tttcaaaagc  21060
ttcagaatct cttttctaat agagaactga tagaaattgg atgtgaggat aaaaccctag  21120
ccttcaaaat gaatggttac atatccaatg caaactactc agtgaagaag tgcatcttct  21180
tactcttcat caaccgtaag ttaaaaagaa ccacatggga aatccactca caggaaacac  21240
ccacagggaa ttttatggga ccatggaaaa atttctgatc cataggtttg attaaacatg  21300
gagaaacctc atggcaaagt ttggttttat tgggaagcat gtataatttt tgtcctaagt  21360
ctgtgctcag ccctcccaca tgtgctcatt gctggttgac tgttggagtc tggttcttac  21420
ctctaagagg aagcccagga gagggcataa agccagcaca ctgtcctcac ctgatggtgt  21480
cagagtcctt acgagtaagc cctagccaga acattgctgg aagagatcaa gggccactgt  21540
ttgaaattgc acagcaggat acggaaaagg ggtaccttag gtataggcat tgtcattaaa  21600
gaaattgcta agatacttga gattttcctg tttaaggaat gagctttatg atacaaagag  21660
cagttctaaa aattagggag ggaattaact aaattaatta ggatatttct caaattcctt  21720
tacagttttt gtctctctgc tgatatagtg tttacatgat tgttatttac taaacaaatg  21780
ctattttgta ttgtgctcct tataacttaa ttgtttatta caaggttttg atggtgacct  21840
accaacaaca agtaatccca aacacagtct gaatttttg ttttccatcc agaaataaga  21900
tgaatctttc catttccgtg ttttcagttt tcatcatttt tatcctatag gttacttatc  21960
tttattttaa agcatttcat aataatttta tagtttttgt tttgtttgct tgtttgctgt  22020
tggaaatgga atattccctc cttccattta gactgctaac cagctgtaaa tgtttcaaaa  22080
tatgcatgtt ttacagcagt tgttcaaagc aatacaggaa cagtaaggac agagccagtc  22140
attttacaac cacattctgt taaactgatg tctattagca gggtttttcc tattttatta  22200
ggaaggactt acacctgata tataacaaag cttgttttaa tcaaggctca gaaaatgttt  22260
ttcattagtt tttttcctaa ccatgaagaa taactgcttt gtaacacaca tgctggctat  22320
aaagcagaca aaaaattcac tgtaggtgct gcctgactgg cctctgtccg tgtttctgtt  22380
ggggctgctt accacagcct ctgcattatc attagctagt gtgttcacaa taccaagttc  22440
ccagtagcaa agaaaggtca agctcttacg catgccattc atttatctac actgtgcagg  22500
cgcactcagg tggcagggac aaagaccact cctttggcgc atctcaagtt cagaattctc  22560
```

```
agtagagggg ctccagctgt ccttttgtca ggtgcccatg cctgctccag gcctgtgtgg  22620
tcaggacacg tgttacagag tacagtgaca ttaatgatgg ggccatggat atggtcagca  22680
ctcagaggat gttagtctct tcattgataa agtcacaacc acttttcctg ttggaaataa  22740
aaagatttga cgtatccttg tctacagcaa cacaggacaa cagataatca gcaggtcatc  22800
taaatctgtt cagagagaaa ggagagctgt ttcctgaaaa tacatcttcc cctgatttta  22860
gtcttatttt tttctgcctt tattgctttc taccctcttc aaaccagcct catttcctaa  22920
attaccttga atatgcattg acacttgtac tgcctgaaat tctggaaaac tcagtatggc  22980
tactccaccg tcagaacttc ctgagcaaag ttagttgctc tctcggctca ctgttttgtt  23040
ttgttttgtt ttcctgcctc aggtttattt gtacaaatag cacaggagga ccagccccat  23100
gcagatggta gcccaggggc gggggtaggg ggtcacacca gtccttctgt cctcatgttg  23160
gcagagatat ctactctgaa gcctttgtag gggcctgggc acctttggga gcctgagctg  23220
gaactgaagg tggagctgca gcctgggcct tggtttgatc cttggccttg gcctttggcc  23280
ggcacagcct gagccccttg gcaatacggg cacgagcacg cttcccaagc ttgggatggg  23340
caatgtaggc aagtcgatcg agcttgcggc tgacaccctt tgggatcttg ggcttaacct  23400
ccttgggctt tacgagggcc ttgatagcct cggcacgtgc actcatggcc ttggcattgt  23460
tggcctgcat cttctttagg cccttcttgt tgtgcttctt ggcaaagtgc atgttcctca  23520
ggaacttggg gtccaccccc ttaagagatt cgtatctttg tgatcggggt ttcttgatac  23580
catttctgtg ccattttcgg gactggttgt gtgtggtgtg gttcttggac ttcgccatgt  23640
ctacacctta agccgcggct cccgaagcac ctagaaccgg aagagttggc tcactattta  23700
gcacacacac acgtctataa tagtgctggc cacttggggt tggaattagt ttatttatca  23760
gcatgttgtc tcccagcact tggtgtgtgt gatatgcagt atgtatttgc agaatgaaaa  23820
gtctgagggc tgacatcata tttcccactg tgcccagaaa gagcacagtt agtccacatg  23880
agctaatggg ggcaaaggga agtgaggagg gagaatgtac tgccttatca tgttttctat  23940
tacttggctg aagtaaaaca gtcccaagcc gatagtaaga tagtgggctg gaaagtggcg  24000
acaggtaaag gtgcaccttt cttcctgggg atgtgatgtg catatcacta cagaaatgtc  24060
tttcctgagg tgatttcatg actttgtgtg aatgtacacc tgtgacctca cccctcagga  24120
cagttttgaa ctggttgctt tctttttatt gtttagatcg tctggtagaa tcaacttcct  24180
tgagaaaagc catagaaaca gtgtatgcag cctatttgcc caaaaacaca cacccattcc  24240
tgtacctcag gtaatgtagc accaaactcc tcaaccaaga ctcacaagga acagatgttc  24300
tatcaggctc tcctctttga aagagatgag catgctaata gtacaatcag agtgaatccc  24360
atacaccact ggcaaaagga tgttctgtcc cttcttacag gtacaaggca cagttttcct  24420
tcatttattc actaatttag cagaacctca ctaagagcct cctatatgcc aggctctgcg  24480
ttagcaataa aaggaatgcc atgcctcacc ccatcaggag gtgctgatag cttgtaggcg  24540
gagtggaaac agatgtgctc tagaggctct aaatattact tctgctgggg tcagttggga  24600
agccacaaca gctactgttc atcttccata aaagacaatc agccgggcac agtggctcac  24660
acctgtaaat cccagcactt tgggaggctg aggtgggtgg atcacaaggt caggtgtttg  24720
agaccagcct ggccaacgtg gcgaaaccct gtctctacta aaaatacaaa aattagccag  24780
gcatggtggc gggcgcctgt agtcccagct actcgggagg ctgaggcagg agaatcgctt  24840
gaacctagga ggtggaggtt gcagtgagct gagactgtac cactgcactc cagcctgggc  24900
```

gacagagcga gactccatct caaaaaaaaa aaaaaaaaga ctgggttctg ttctgtggag 24960
gttcttgtct taacatatcc actgttgatt gcccagatgt tgatgtaatt aatttagcag 25020
tcgtaaatag tttagcactt gcattaaata gaccaaaccc catagtaggt atttgaaata 25080
cagaataaat gtgaggtacc cctgctctaa aggagtttat agtccagagc tgacttatgg 25140
aggatttctt tctattattt ctgggtctgc tactaatttg tctatttcat atcctaatta 25200
tccttgtttt cattttgatt gaaaggggga gagcatagaa attgtggtaa aaggtagttt 25260
tattttttat ttgagatgga gtcttgctct gtcacccagg ctggagtgca gtggcacaat 25320
ctcatctcat tgcaacctcc acctcccgcg ttcaagcaat tctcctgcct cagcctcccg 25380
agtagctggg attacaggtg tgcaccacca cgcccagcta atttttgtat ttttagtaga 25440
gatggatttt accatgttgg ccagtctggt cttgaactcc cgacctcagg tgatcctctc 25500
actttggcct cccaaagtgt taggattaca ggcctcagcc actgcaccca gcctaaagtt 25560
agttttagat taagtgtttt catgttttcc cttgcaaagt aataaactgg tcaagttatc 25620
accttgttcc atctccatat taatcagggt ccaaacagga gatagaaacc atgcaacaat 25680
ttgagtagtt gaataaagaa ttataaacag gagattagag taatagggga ttagatagta 25740
agaggtgaag agataggaac agcagatata aagaacaacc atttcctcct atggctgaga 25800
taccatcccc tcaccacact cccccaccta ctcactgaga tgcagacctt attgaagaga 25860
atgtaactgg cttgctgcga ggtaaagtca atgaggcgct ccccagtacc actctgaggg 25920
gatgctgggg aaaactgccc atgagaagag ggcacatgct gctggccact tgtgctaaag 25980
aacttgaagt ctgataggag tgcaccctaa cctggcatag aaaccctttc ttcctgctga 26040
gtccctctag caccttatac tggcaaagct ttacattgca aacctccatt atcacagagc 26100
aagcaatgaa agatggactc agagctgagg cgataaattg atagctagca tagcctctaa 26160
actgactttt atgactacat tttatggata gaaagtgttc ttatatatat tgtttcttta 26220
cataataggg gacttattca tggctgcaga tgagaaaaca gatcctaaga agttaagtga 26280
cttgcccaag gtcacacaaa gaattccact agttctaaaa tgacagtaat tacagttaac 26340
atacattgta tgtggcagat acatataaag cacatggcat taattttttt ttttgagatg 26400
gagtcttgct ctgtcgccaa gctggagtgc agtggcacga tctcggctta ctgcaacctc 26460
tgactccctg gttgaaggga ttctcctccc tcagcctccc gagtacctgg gattacaggc 26520
atgcgccacc acgcccagct aatttttgta tttttagtag agacgtggtt tcatcatgtt 26580
ggccaggatg gtctcgatct cctgaccttg tgatccaccc gcctcggcct ccccaaatgc 26640
tgggattaca ggcgtgagcc accacgcccg gccacttggc atgaatttaa ttcccgccat 26700
aaacctgtga gataggtaat tctgttatat ccactttaca aatgaagaga ctgaggcaaa 26760
gaaagatgat gtaacttacg caaagctaca cagctcttaa gtagcagtgc caatatttga 26820
acacactcag actcgatcct gaggttttga ccactgtgtc atctggcctc aaatcttctg 26880
gccaccacat acaccatatg tgggcttttt ctccccctcc cactatctaa ggtaattgtt 26940
ctctcttatt ttcctgacag tttagaaatc agtccccaga atgtggatgt taatgtgcac 27000
cccacaaagc atgaagttca cttcctgcac gaggagagca tcctggagcg ggtgcagcag 27060
cacatcgaga gcaagctcct gggctccaat tcctccagga tgtacttcac ccaggtcagg 27120
gcgcttctca tccagctact tctctggggc ctttgaaatg tgcccggcca gacgtgagag 27180
cccagatttt tgcctgttat ttaggaactt tctttgcaag tattacctgg atagttttaa 27240
cattttcttc tttgaaccta gttataaagg tattgtgctg ttgttcctag gcttagagtc 27300

```
ataaggcctg agctcacttc ctcactttgc ctccatctgg aaccttagac caacttccta  27360
ggaaaacgag ctgtctgaaa acagaatagg gtgcctcttc aatgtgctct tcactggaga  27420
tgttcaggag gaggctactc ccacctacac agggtgcagt ggagggtctg ggccccaggg  27480
aggcagcagg aagagtggaa agagcggagg ctctactgtt ggacagacct gggttaccag  27540
ccgtgtgact agccttccct ggcctccata tccccctcag taatgaagga atgtgtcatc  27600
cccaaatcca gggacagtta caagcagtca gtgaacagaa agtgtctggt acaggttcta  27660
agtgcttatt attctaagtc acttcactta cctgagttct cagttttcct atctataaga  27720
taagcaggtt ggataaaatg ttctccaata tactcctggt cctgagatga tgtgattgtg  27780
ggcagccctt taatcatggt gaagatgttc atcataagca cactgaaact acaaaatagg  27840
aatataaata ttttctccat taaattatgc tggatcctag aagcaaaaac tggaactgtg  27900
aaaccctact tcacagaaaa cttaaaattc ccaagcagat gaatgcttct cggaaggaca  27960
ctgacagtta cctacctgga aagaatctag atggaggtgg catgggcact aagcggtgag  28020
attaaaccca gttagggcag ccccaccagc cttggaaccc acacatctgg agattgttga  28080
tgcagagaga aaggttccta ctggtgagac ctgaaaggga tatgtggcag gtgggaggaa  28140
gaagttctgt ctggaaacca acccttgttc ctccgttatt gattgactcc tggtaccaac  28200
atgagcccta ggtcttatag aggccataag tccctatgcc ttatagtgcc catggatgag  28260
atgaggccac acatgccccc agtgggttaa catgtctagc gtgggtaagg ctcttggagc  28320
actatgatac acaggaaatg cccagtaact cttagttggt ttgatatctg ttcccattgc  28380
tcacttaagc tcagtgcccc tttactgatc cttttattct gcctccctct gcacatgtgc  28440
attgagactc ctatctgaga cacacactgt gttgggtgcc cagggatgca gcatagatgt  28500
tgctgccttc cacagaagcg ctcatggtct gctagagaat atatcccatg ggagagaaaa  28560
acagactcgg gagaatatag caggggccct tgtcctggac tttggcagtt aggaaaggga  28620
gggaagagac atggaggctg ggacccaaag gctaaatagg aatttgctgg gccaaagggg  28680
agggggaatg aaaagagtgt ttctggcaga ggaaatggca aggataaagg cctggaggcg  28740
caagagaata tgtgtttgag gatctgaaag ttgagtgcag tgggtccagt gttctctacc  28800
ctggctgcca ttagaattac ctgggaaact tttagaaaat tccagtgtct gggccctccc  28860
taaaacaata aatcattctt gggtggtggg gtctgggcat caggattgtt taaaaccctc  28920
cccaggtact gtcatgtgca gctggggtta agctgtgctg ggtctgagt atggatctgt  28980
tagggcaagt ggcggtgatg gagttgaggc tgcagaattc aggccaaata gagaggtttt  29040
catcaggata ttaaagagtt tagatttcaa tttggtggga atggatggga tcttatttgc  29100
attttatgaa gagctccctg gttgcaatat cagaatggat tggagaggag caagatggaa  29160
gcctacagtg atttgggaga agtggtgagg gacttgagac acaggaagta gccccattca  29220
ctaatagttg agtatgtaga tttgctagga cctggaaatg gtttggctgg tggggagtgg  29280
gaagaaaggc ccaaagtgtg aaatgaagat ggagagcaca ttgcctagcc cagagtgatt  29340
gccatttgct ctgtcccagt tgaggtccaa ggggttggcc agagatcatg gagtctgtgg  29400
ctccatgggg agaagaacct ctcagcatgc ctccttgtct tatcctgggt tagtcagatt  29460
cattttgtta gattacattt tttttccagt ggaactctgc ttaagtcctg accagtatgt  29520
tttcagaagg atcagagggc ctgcccttgt ccattggtgc atgacaccag cttggtgggt  29580
tccttgctgc tccctgtttt catagggtta tcagaatacc ttctctccct gccaccagca  29640
```

```
ggtcacactg gctcctgact ttttggccca tggaaccacc atctttctgc ttcttagatt  29700
gtgccttgta ctccactgat catggccagt acatcagaag ccctggtttg cagtgaatgc  29760
atttgatatg gaaatcagga accctgggga taccactcat catatttggt tgctgtgttt  29820
ttcctccaat ctttcaccat aacaacaatc aactcaaaag atttctataa ccacttgtgt  29880
gggggtttct ccccacacac taaacaagca gtcagttcca gagtggacag cagctggtct  29940
cctccaattt aattccaaca ctgtctactt ggagatagca ttagatccca caggttgagg  30000
gtgcagtccc ctagactgcc cccagtctcc tgcttcagac accagtcaca agtccaggac  30060
tctagaagtt ctgaccagtt tcaagttggg gttcccacaa ccccccactt tatttttgat  30120
taatttgctg gagtggctca tagaactcag ggaaacactt agttttctgg acttattaca  30180
aagatttaaa aagataccaa taaatagcca aataaagaga tatacagggc tagatctgga  30240
agggtctgga gcgcaggagc ttctgtcccc atctacttgg ctcccagcag atggatgagt  30300
tcttattcat tttcttgtca gcttcgacat gttcagctct ctggaagccc gcaaactctt  30360
gtcttcttgg gccttttatg gagacgtcgt taggcaggca tgattgaaac atggacaact  30420
gtgtcgaaat atgattggac ataaaggggt ctaaactcag tgaggcctgt ttgttcagat  30480
tcttcttggc ctctctgtgg ccattctttc ctccaggata tggggcagga cccctatgga  30540
atgagggtct tatgacccac aatcaaatta gagtcctgcc ttgggcaagt gaaaggaaag  30600
caggagaagg taagagaaat tctgttgcct aagaccttct gaggcctaaa gcaccccaac  30660
attataacag aagacgataa caggactatg ggagttatga gctgggaacc ttggacaaaa  30720
atatatacat attaaataaa tattaagtgt atatatatac ttacgtatat taagtgtatg  30780
tgtgtgtgtg tatatatata ttttttttaat ttactggttg gttttgggaa gcagaaatta  30840
ccataactac tcttaaaaat cttttaagtc tctttgaagt tagaaaagtc actgtacctt  30900
tttgtttcca ttggccctgt acttcttatt ataccccagc aggaggagca taatgtgttg  30960
ttatatcatt ctggtgataa gattcataag tgggttcagc tggtgacagc ctgattccct  31020
cattgtaaac ttatccatca acatgtagct taatcgtttc accttttgtg atgaccatta  31080
cctgaatcag ttatttcatt agattgcaag attatgcttt tctgatttta tcatttcttc  31140
tgtattgact gtaattcttt ggtatagaag aactttccct tgttaatagc tatttggttg  31200
tcctgaagta cagttcttac tagaaagtaa gaccaaatgc tgaattatat ccctctagct  31260
atcaattttc gaaggaatga atggtgtcct agtaatttcc agtggtgttt aattacgttt  31320
tcccttctct ttctccttct cttattccct ccctctccat ctcctccctc ctcactttca  31380
gttttttgct ctttcagtat tttgtcatag ctgttaacag agcaacatat tttaatcaat  31440
tgtagtcatt tttctttttg gtgctcaaat tatcccgtct tagtcccatg gaagcaagcc  31500
cttggagcta gggccctcta ccttttgatg gatttccatt tgtcttgata atttccttgt  31560
ttctgacaag acaagatgtt gcaggcacat tttatacttt cccagcccaa accctggaat  31620
aggccttttc tccgaggagc tctagttcat tttagtggga aatggtattt agagactata  31680
atctgggatc tgggagtcct cattgctact gagtagtcat tacttttagg cttttccagt  31740
ggtcagagct aggaaatatg tatatttaaa aatggacagt tgaatggttg ttgccaggag  31800
ctgggaggaa ggggaagtga gaaattgttt aatgggcaca gagtttcagt ttggggaaga  31860
tgaaaaagtt ctagagatag ctggtggtga tggttgcgca acaatgtaaa tgccactgag  31920
ctctcattta aaaatggtta aaatggtaaa ttttatatat attttaccac aataaaaaaa  31980
agtcttcttc tgggagcacc cccccaagac aaaaatatga aaattttaca ctgatacttc  32040
```

```
catttcaaga taattttaag attataagga ttttgcttaa ttcttgaatt ttatacctgt  32100
aaacctttta tacttcaaat ttcgggcaga attgcttcta taacaatgat aattatacct  32160
catactagct tctttcttag tactgctcca tttggggacc tgtatatcta tacttcttat  32220
tctgagtctc tccactatat atatatatat atatatatat ttttttttt ttttttttt  32280
aatacagact ttgctaccag gacttgctgg cccctctggg gagatggtta aatccacaac  32340
aagtctgacc tcgtcttcta cttctggaag tagtgataag gtctatgccc accagatgga  32400
tcgtacagat tcccgggaac agaagcttga tgcatttctg cagcctctga gcaaacccct  32460
gtccagtcag ccccaggcca ttgtcacaga ggataagaca gatatttcta gtggcagggc  32520
taggcagcaa gatgaggaga tgcttgaact cccagcccct gctgaagtgg ctgccaaaaa  32580
tcagagcttg gagggggata caacaaaggg gacttcagaa atgtcagaga agagaggacc  32640
tacttccagc aaccccaggt atggcctttt gggaaaagta cagcctacct cctttattct  32700
gtaataaaac tgccttctaa ctttggcttt tcatgaatca cttgcatctt ctctctgcct  32760
gacttgccct ctggaatggt gctggaatgg tcctgtggcc ttgtccactg tctgcctttg  32820
accataactt gaaagtcacc caccatagtg tcctttgaaa taacttaaat gtccacagtt  32880
ccaagcatga gttaaaaaca cttcagaatg tagagtagtt gttcaattga ataaacacac  32940
acaccagaaa aaaaagcaag tttatctttt atttttagta aagaattttg atagagcctc  33000
aacaccagaa atggctagag agagaagcct aacatatctg gaggattatt tttcatccta  33060
cttaaagctg ctttcacttt tttcaggaaa aaacacacgt tctgaatcta atttataaaa  33120
ctccctggcc gggtgctgtg gctcacacct ataatcccag cactttggga ggctgaggca  33180
ggtggatcac ctgaaatcaa gagttcaaga ccagcctgac caacatggtg aaaccccatc  33240
tctactaaaa atacaaaatt agccagacgt ggtggcgcat gcctgtaatc cccgctactc  33300
gggaggctga gacaggagaa tgacttgaac ccgggaggcg gaggttgcag tgagccgaga  33360
tcgcgccatt gcactccagc ctgggcaaca agagcgaaac tccgtctcaa aacaaacgaa  33420
caaacaaaaa ccccaaaaat ccctgaagta cgtgagctag tggtgaaaga aagctggaga  33480
aaaggagcag gaataataat aataataata ataataataa agattgtcat ttaattttga  33540
gtacttccag tgtacacttt gcaggtactc taagacatta cctcactgaa atctctaagg  33600
tagatattct ttatttaaag tgtacttgta tgaaacctgg agctcaaggt gaaggaattt  33660
gcccaaggct gcacttgcac tatcgtggca ctaattagcc gtgtgaactg ggacacgtta  33720
cttcagtttg ctcatttctg agtcagccta gcaagatgac ttctaagaat tttttccagc  33780
cgggtacatt ggcctgtaat cccagcactt cgagaggcca aggtggaagg gtcacttgag  33840
tctaggagtt acacacaaca cacacacaca cacacacaca cacactagcc aggcatggtg  33900
gcaaatgcct gtagtctcag ctactccgga ggctcaggtg gaaggatcac ttgagcccag  33960
gaggttgggg ctgcagtgag ccatgatcac gccactgcac tccagcctgg ctgacagagt  34020
gagatcctct gtctcaaaaa aagaaaaaaa aaaagatttt tttccaggga ataataaagg  34080
aagctaatat ttatggagca tctacggtgt gccaaatact ttgcatacgt tatctcattt  34140
aatgctctta tccctgcagg gaaagtatta acatttgttt atcacttgca gaactaagtg  34200
atatttacca cagagtagac aaatattttc aagcccaaaa tcaagtggta tcacttttct  34260
gctgagaatg tttcagtggt ttcctttgct cttgggataa aacttaaatc cctcacccta  34320
cccttgctcc aaccctccac tttccttctc ccatgtggtg atttggccat acagctcttg  34380
```

```
tggctgatct gaactgactg agctttttac ccttttgctc ttgctgttct tacagcctgg  34440
gaaccccctg gttacctctt ggcttggtgt ggtggcttac atctgtaatc ccagcactct  34500
gggaggccaa ggcggacgga tcacctgagg ttgggagtat gagaccagca agtcacctct  34560
tgccagtggc ctttgtccat tgagtctgaa gttctttctc ctctcatttc cccatcattc  34620
tattatgcta ccttgtttta ttttcttcat tgtgtttatt gatacttaaa atgatctctt  34680
ttctgttgct gtttgactct cccactagaa agtaagcatt gtagatcggg cactgtggct  34740
cacacctgta atcccagcac tttgtggggc agaggcgggt ggatcacctg aggtcaggag  34800
ttcgagacca gcctggccaa cacggtgaaa ccccatctct actaaaaata caaaaaatag  34860
ctgggtatgg tggctcgtac ctgtaatccc agctactcag gaggctgaga catgagactc  34920
acttgaacct gggaggcaga ggctgcagtg agctgagatc acaccacagc actccagcct  34980
ggaagacata gtgagactct ctctcaaaaa aaaaaaaaaa aaaaaaggaa gtaagcattg  35040
tgagggcagg taccttctct gttttgttca ttgctggatg tagttagtat acagcagtat  35100
ctgatggatg gatagatgga ggaatgaatg aatgagactt cacaaattca gctcacttgc  35160
tcaaggccct gcagctctac gggatgaagc tatactccag agtcctgcta cattggctgt  35220
gtggccagct gctgggatct gagggttgtc agataagcag tctaccagag aacagactga  35280
tcttgttggc cttctgccag cacaggggtt cattcacagc tctgtagaac cagcacagag  35340
aagttgcttg ctcctccaaa atgcaaccca caaaatttgg ctaagtttaa aaacaagaat  35400
aataatgatc tgcacttcct tttcttcatt gcagaaagag acatcgggaa gattctgatg  35460
tggaaatggt ggaagatgat tcccgaaagg aaatgactgc agcttgtacc ccccggagaa  35520
ggatcattaa cctcactagt gttttgagtc tccaggaaga aattaatgag cagggacatg  35580
agggtacgta aacgctgtgg cctgcctggg atgcataggg cctcaactgc caaggttttg  35640
gaaatggaga aagcagtcat gttgtcagag tggccactac agttttgctg ggcaagctcc  35700
tcttccttta ctaacccaca atagcatcag cttaaagaca atttttgatt gggagaaaag  35760
ggagaaaaat aatctctgtt tattttaatt agcattaatt ggtattcttg ttaaaccata  35820
ggagtcagag taaatcagcc atttcaccaa ttttcagttt gtttctgtct tagctaacag  35880
cagtgtaatg gtcagcaaaa ttcttatctt gtgtactgaa tggcatgtcc tgttgctgaa  35940
agtgcacagg cttgggaggt agccatgagc tcaaatcctg gcactaccac ctctcttgtg  36000
tgaccttaga ctcctgacct ttctatgcct cagttctttc ttacctataa aatgaaatta  36060
attttaccct taaagatcat cgtgctgatt agagataaaa tataaataat aacacttgtt  36120
acagagcaag gagttgacac ttttatattc tgaagacaaa gtggtaaatc attatcatct  36180
atgtcagaaa tagcttttga gaatacctga gtatagaact atcttgatcc ctgttacttc  36240
aaaactaaaa taatggtttt aggaattaaa aggtgaggct agtcacctcc aagggatgaa  36300
ctgactcagg gattgaggta tataacagtg aactggtcca aacaacagtc ctgaccccac  36360
tttatgagtg agactatgag taatggtcta agtgtagaca tcattgtcca gggctccagt  36420
aggcagctct gtacttgaga atttagcagt gacccttcta tttttcatct attatacctt  36480
tttttttttt ttttttgac acagggtctc actttgtcac ccagctggag tgtggtggtg  36540
caatcatggc ccactgcagc ctcaacctcc ctgggcttag gtgatcctcc cacctcagct  36600
tcctgagtag ctgtaattac aggcatgtgc catcatgccc agctaatttt tcttttctta  36660
gaggtggggt tttgccatgt ttcccaggct ggtcttgaac tcctaggctc tcacctctgt  36720
cttccaaagt gctgggatta caggtgtgag ccaccacacc tggcctatta cacatttctt  36780
```

```
aattaaagta gtcaaatttg aaaactgtta caaagtgtat cttaaaatac gacgatctgg  36840
tttaattttt aaaagatatg agtagccaag gagcaattct gtgcctttcc cactagtccc  36900
taacctttta aagcagctgc ttcttggctg ggctcagtgg ttcacccctg taatcccagc  36960
actttgggag gccaaggcgg gtggatcatg agtcgagatc atcctggcta acacagtgaa  37020
accctgtctc tactaaaaat agaaaaaaat agctgggcgg ggtggcggat gcctatagtc  37080
ccagctactc gggaggctga ggcaggagaa tggcatgaac acgggaggca gaggttgcag  37140
tgagtcgaga ttgtggcact gcactccagc ctgggcgaca gagcgagact ccatctcaaa  37200
aggaaaaaaa aaaaaaaaac ccatctgctt ttgattcagt ggcttcttta attttgtcgg  37260
tctcagtcac catttgtcta agcaaattca ggcaggcttc accttgcctt tctacatttg  37320
ttccctttc ttagcatttt gggcctttgt ttacacgtgg gaaaagaccc acaggtcgtc  37380
tctccctttg ggcaggatac aggcttcctg tgactgaggt tttgctagct gtagaagtgg  37440
ctgccaattg gcttctggtt tttatttcca tgatttgctc cagtggctct tcccttccat  37500
cattgttagc tttcaagcta ggaactttta aaatgctttt aaataaaagt gagctgttac  37560
ttgatgcatt tagcagtctt cctcacagtg gttttgatag acagactccc tcagtttgga  37620
atttatgagt tttctttaag ggtttgtctc cctcatgtat agcaggctgt tgaaagttac  37680
aatgtcaata actttctgaa tagtatcaaa ctgttttcag tgcagtgtat taacaaaact  37740
aacctgcctc aagtttggtc agctttggag tcttactgag gctaaaatga taaatctaaa  37800
tgatttaaaa ttgtgtattc ctacacagta tctcacttaa ttatgtaata gtcttgtgag  37860
tgaggcagag cagatgccgt tttctctatt tttaaagatga ggaaaatgga atggaaaatg  37920
gaaaggacag actaattgca acatcctcgc aatcaaaaac aggcccaggt tcatgccttg  37980
ttggcagtgg gttgctactg gctgtggcct tcatgcagga aggctagatg cataaccagg  38040
tcaacagccc gtgcaggaca agcacgccat gtaattctga ttccatcgac tgaggctggt  38100
gttttcaaac gtgctggtgt agggtcttac agacagagtc atctgtgcta tggggaatgg  38160
aatgtgctct tgctttggag ccagaactcc tctgaagctc ccaccaccta caccattcag  38220
aggccagaca gaaatttgtt caccattttg ggcatgattt tcgtgctttt gtaaaatgtg  38280
cttcactgca gcccttactg ggctgtggtg atgaacactt aagatactgt gtgtgtgctt  38340
tataatctgt aaggcactgt tcaaggggag ggacctctgc catgagcccc tacccactgg  38400
tatctggttg acatccaaag ccccagcctg ggagaagctg attctctagt tgaatgctgt  38460
atagggattt gactgaggct cagatttggt gaggaagacc actaacctta acagaccaac  38520
aggctggcta ctccctgatg aagttcccca ggccatgaaa gaagtaagag atacattcct  38580
tgtaacagct ttcttagttg cacctgtatg attatttgat cagtgtgttg tctgtgcagg  38640
gatcatgtct gtggagctca ccacctcgtc ctcggtgctg agcagagtgc ctggcatgtg  38700
tactcagtag atatttgcta agggagcgag tcagtgattg agaggagcag cctgggaggt  38760
aaagccctag aatctttatt ttaaagggat atcaaagttg aacattcagt tagacagttc  38820
tcttgagtcc agggatttac ccatccatgg tggacacact ttcagttaaa aagtaaggtt  38880
aattttgaca ggttgcagta tccaggcaag cattctatgg aataaggctc atctcaggga  38940
ttagtaatga ctgaattaac ttactgctag tcccataatt ttgacgttaa ttaatggggt  39000
taagaaatgt cataagctat ttggtaccat ttaaagtgaa aataccctta acgtttttg  39060
cctccagata tccacactta atttcatttt cttgctcttt ggtgaacagt cctgggtctg  39120
```

aatgtatata tccatggttt gtcactaggt gacaggtttt tttggaacaa gaaatcagtt 39180
cagtgaacat ttgtcaagta tcttctctgt aaaaagtgta atgtgccaag ctcagaagta 39240
ggaagtgaaa tggataaact atgacccctg ccttaaagaa caccatggtg ttgtatggga 39300
attgtttagg tagaatgaaa gaaatcctct aatagagata tgaggccagt tcagcagaaa 39360
gccagggtga gatctcctga gagggatgga agggtgtctt gatcatctct ggtagcagca 39420
aaggcactgg catacagtgg ccactggaag acaaccagca ggggatgggg gcgtttaccc 39480
ttgcaagtga gcattaggaa ctagaggact gattgccctt tcttcagctt tggtttccct 39540
tgctgcagaa aaagatgctg agactcatgg cctcggttat gaactcagat atgtggtttg 39600
gctttgaagc acagatggat tttgtccgat tttggcaggg aaatgcctac agacagcact 39660
atgggcatat ttaggttagg gacgaaatgc aagttgatta agtcctgata agaggctgtg 39720
aagaggtcca agaagcctca caatgcccaa tgaagaaaag ccctgtgctt ggtgctgccg 39780
cctcccttcc ccgtcctgct ggcagggctg cgcttcagta gctctggatg cgtcagagca 39840
gtccatgaac attctgtgtg gaaaatctct gactgtttta gtggattaca ctgctctccc 39900
tttcctccag tgcctcgtta ttcagtatta tttgatgttc tccagctttt aaaataatca 39960
ttttccgcct acgcagaaca tcctgtagag acgttgaggt tccagtggga acagagagga 40020
atacttattc taaaaatgaa gaaaataaac cttttttat ggagtgggtg atagtattgc 40080
agaacttcta taatagtatg agaattcact tgtggtgcca aagcttaaaa aaaaagtata 40140
gtaaaaacat aatgtatagg cttattgctg tgctatgacc catgccccgt tttctccaac 40200
ctctcttgtc ctcactcttc ctttttgctg gtgatatttt tacttatttc atgaaaaaaa 40260
agataacata tacacacaca tagatatatg cacaagtata tgtatatatg tgtgcataac 40320
acacataaac atatacattg gtaaatttaa aaacatattt atgaaatata tgtagcatct 40380
acagaaaaac atgaacactt gtgagaatag catctgccta aaaaatagga catcaccatc 40440
acctttgagg ctcttatgtg ctgctcccct gtgccattcc cttcccttct tccttagagg 40500
tgattactat tctaaatttt gggattatta tttccttttt ttattatagt gttttaatta 40560
cagttttatt acctgtattt gtattcctaa aaatttgttt acttttgcaa gctttagatt 40620
ttataaaagt agaattacac tgtaagttta atttttctgt aatttatata tagctacaca 40680
tatattccta agattcatcc atcttgttac atatagctct ggtttacctt ttctgtataa 40740
tatagattct gcttcgtgaa tttacagttc attcattctt ctgttaaagg acagttggag 40800
gactcatatg gcctcagtct ctgtgtcccc acatgccacc ctgcttccca gcctcatatg 40860
agttgattgg tggcctggca tactggatga gaagctctag gtcatatatt taagagagtt 40920
attgctgggt cataaaatga cagattgttt tccagagggg tcatattgat ttaaattatc 40980
accaacaatt atattgtcag atttttacca gtttggtgat tgtgaaacag tgtctgatgg 41040
tagtttttat ttgcattttc ttggttgaaa taaagttgtg tatttcagcc aggtgcgttg 41100
gctcatgcct ataatcccag cactttagga ggccaaggtg ggcagatcac ttgaggccag 41160
gagttcaaga ccagcccagc caacgtggca aaaccccatc tctactaaaa atacaaaaat 41220
tagatgggta tggtgtcaca tgcctgtaat cccagctact caggaggctg aggcacaaga 41280
cttacttgaa cccgggagat agatgttgca gtgagccgag attgtaccac tgcactccag 41340
cctgggcaac agagcaataa ctaaataaat aagtaatcaa ttaataaata agtatatttc 41400
ctcagctgtt aagtacctgt tcaagttttt tacccaatat ttgatgggct cttttttttgt 41460
cttttctaat taatttttgg agtttttgat atattctaga tagtaatgag ttacatgaaa 41520

```
atatccctag tttagggatc ctctagtaac tttttaaaat gaatacttgt tttaggaaca  41580
gaaattctta gatttaatgt aggcagattt tatcaattgt tctttacaga ttggctttgt  41640
agcttaagaa atccttccta actttgcaat aattaaagat atgctcttag attgtttcct  41700
aaaagactga tacttaagcc tctagcccac ctggaattga ttttcacaga tactacattt  41760
tttactagtt atagattggc cccttcgtag agcaagtccg atagctgcca tttttatggc  41820
agcatgtgct cacttagtgt ctctgtcaaa ttttggtaat tctcacaata tttccaactt  41880
tttcattatt actatatctg ttatggtgat ctgtgatcac tgatctttgg cattactatt  41940
gtaattgttt ggggcaccat taagctcact gtcttatgtg ggcataaacc atgcccacat  42000
aagacagtga gcttaattaa taaatgtgtg tgctcagacc cctccactga ctgggtgttc  42060
acatgtcttc cttactctcc tcaggcctcc ttattccttg agacgcaata atatggaaac  42120
taggcaaatt aataacccca cagcgtccac aagtgtttaa gtgaaaggaa gaggctgggc  42180
gcaatggctc acatttgagc tcacaaatga gcccatgctc atttgccatt ccaaaaatcc  42240
cagggccctt aagaattatg ctaactctac tctgcctctg ctctataaat ggaacaacaa  42300
agcctagatg acagcacatc tttttagaac atgatttact gaatatttta agcccattgt  42360
ggagacctac tgctcagaaa aaaagattcc tttcaaaagc ctgtaatccc agcactttgg  42420
gaggccaatg caggtcgatc acctgaggtc aagagttcga gaccagcctg gccaacatgg  42480
tgaaacacgt ctttattaaa aatacaaaaa ttagccaggc ctggtggtag atgcctgtag  42540
tcctggctat tcaggaggct gaggcatgag aatcacctga acccaggagg tggaggttgc  42600
agtgagccga tatcatgcca ttgcactcca gcctgggcac cagagtgaga ctacgtctca  42660
aaaacaaaac aaaaaaaaaa aactgaaagg aagagcttaa tgagaaaggc atattaaaag  42720
ccagtatagg ttgaaagcta ggcctcttgt gcaagttagc caagttatac atgaatggta  42780
aagcaaaaca gctttattgc tgtaataaag aaagttttag tggtctggat agaagatcaa  42840
atcagtcaca gcattcccct aagccaaagc ctaatccagg gtaaagccct aacttgcttc  42900
aattctttga agactgagag gggtgaggaa gctacagaag aaaacttgga agccagcaga  42960
gattgatgag gtttaaggga agaagccaca agtgctgatg tagaagctgt agcaagttat  43020
ccaaaagatc taattgatga aggtggctta cactaaacaa cagattttca atgtagacaa  43080
aacaatcttc tattagaagg tgtcatctat gacttacata gttaaagagg aaaagtcact  43140
gcctggcttc aaagcttcaa aagacaggtt gactctaata ggtactaatg catctggtga  43200
ctttaagttg aagccagtgc tcatttgcta ttccaaaaat cccagggccc ttaagaatta  43260
tgctaactct actctgcctg tgctctataa atggaacaac aaagcctaga tgacagcatc  43320
tttttagaac atgatttact gaatatttta agcccattgt tgagacctac tgttcagaaa  43380
aaaagattcc tttcaaaata ttactgctca ttaacaatgt acctggccac cctagatctg  43440
taatggagat atataaggac atgaacacta acacagcatc cattctgcaa cccatggatc  43500
aaggagtgat actgactttc aagtcttatt taagaaatac atttcatagg gctctagctg  43560
ccatagatag tgattcttct gatggatctg agccaagtaa attgaaaacc tctggaaaga  43620
attcatcatt ttagatgtcc tgagaaacat tcgagattcc tgggaagaag tcaaaatatc  43680
aacattaaca ggagtttgga agaaattgca tccagccctc atggataact ttgaggggtt  43740
caagacttca gtggaggaag tagctgcaga tgtggtggaa atcacaagaa aattagaatt  43800
agaagtggag cctgaggata tgactgaatt gctgcaatcc catgataaaa tttgaacaga  43860
```

-continued

```
tgaggagttg cttcttatgg atgagcatag aaagtagttt cttgagaaag aacttaattc  43920
tggtgaagat gctgttaata ttgttgaaat ggcaacaaag gatttagaat attatataaa  43980
cttggtaaag cagcagcagg gtttgagtgg attgacacta gttttggaag aatttctact  44040
gtgagtaaaa tgctatcaaa caacatgaca agctacagag aaatctttca tgaaaggaaa  44100
aatcaattga tgcagcaaac ttcactgttg tcttatttca agaaattgca acagcttcct  44160
cagccttcag caatcaccac cctgatcagt caacagccat catcagggct agatcctcca  44220
ccagcaaaaa gataacaatt cgccgacagc tcagatgact gttaccattt tttagcaaaa  44280
accttttaa ttttatttat ttatttattg gagacagaga ttcactctgt cgcccaggct  44340
ggagtgcagt ggcacaatct cagctcactg caaccaccac ctcccaggtt caagtgactc  44400
ttgtgcctca gcctcccaag tagctgggat tataagcatg tgccaccacg cctggccaat  44460
ttttgtattt ttagtagagg caggatttta ctatgttggc caggcttgtc tcgaactcat  44520
gatctctggt gatctgccca cctcgggttc ccaaagtgct ggtattattg gcatgagcca  44580
ctgcgcccgg ccagcaaaaa agtgttttta aattaagcta cctacgttga ttttagacat  44640
aatgctattt gcacacttaa tagattacag tgtggtgtaa acataagttt tatatgcact  44700
gaaaaacaaa aaatttcaca tgacttgctt tattgtgata ttgactttat tcctgtagtc  44760
tggaactgaa cctgcaatat ctcagaggta tgcctgtatc tacttgttct gtgatacttg  44820
ttattgtcag tttgtttgga tttaccacat attatttgat cataattctt tcctgtagat  44880
gttttatggt ctgcctaaac ctttagtggg gcctttgatg gcttagtcct ttcaggctta  44940
agacaataga agtttatttc tcagagttct aaaagctggg aagtccaaga tcaaggcacc  45000
gacagattta gtgtctagtg aaggcccgct tcctcataca tggcaccttc tagctgtatc  45060
cttacatagt ggaagggaat agctagctct ctggagtttc tttcataagg gctaatccca  45120
ctaatcccaa ttatgaggga agacctaatc acctcccaaa ggccccacct cctaatagta  45180
tcaccttggg ggttaggatt taacatatga attttgtggg gacacagaca ttcaaacaat  45240
agccatggca aactttttg ctttgtctaa ttcactctta ttttgaaaag tatttgtgtt  45300
gggtttaaaa ctccagattg gtaattattt tttcttagtg cattgaaggt aatagtgtat  45360
cattttctga tttctactct tgctcttgaa aattcagcta tcaatcttaa aatttattac  45420
ctgttgaaaa tccagctacc agtcttatat tttatttact tagtgggtaa tctctcttct  45480
gagtaccttt aagatctcct ttcagaaata ccatgtagta accctgtgtg tcacgtgtgg  45540
attttgttgg gcttgctagc tgagacttga cagttttcat cacttctggg atattctcag  45600
gtattttgtc ttcaaagtct tcagatattg tcctcttcct gccctctctc cgactccttc  45660
tggaacatga gttatgtatt tattatctcc catgtgcata agttatcttt acatattttc  45720
aatttcttta tctttctgtg ctacattctg gataattttg ttgatctacc ttccagttaa  45780
ttagcttgtt aactttgtca aatctctttt taagtctatc ttgatttttc ttttcaatta  45840
ttgtattttt catttttaaa aactttatgt gctcttttgg aaatcttgat cccaggagat  45900
agtggatagt gtcctgctgc ttactcatgg ttttaatagt tcttgagcat gctgaacata  45960
cttattttat gttatttgct aatctttcca attcctgaaa cctttacaga tctcattctg  46020
tggattcttc tggattctaa ttcatggggc atttttttg ttttttgtta attcctcata  46080
ctttatctgt ggggaattac ttgaagcctg ggttgacaat gaaattctgc agagagaatt  46140
tgcatttgat tctactggag gaacagtcag ccccgatatc agtttaaatt aaaatctctg  46200
cttaaggttt tcaggcaacc tgcttagcat gaatcctggc tggaaaagca tgtgaggacc  46260
```

```
agtttatgat tacacattca cagggtgtca tgttttcttc caacaccaat gctagaggtg  46320
gcagttttgc ttactgccct tggagggaca ggggagtggg catgggcata gtagtatggt  46380
tttccttttc actgggggtg cagcccttgg agtctcagct taatgtgttg gggaagtggt  46440
ctcctattag actctccatt tcaaaccatt ccatgatttt gtcctccttt tgccaccttc  46500
cgagcctgta aaaactaatg tttgtgattc ctgaggtttc tctaatgtct tttaataaag  46560
ttgacctcag agatctcgtt acctctctga gttcctgctt tgtcttagat tttgatcctt  46620
gagtgttctt taatctttta gcaattcctt gttgcatgtt aaaagattag ttatatttta  46680
ttcctcattt gtgttcgttt tcaccaggag gctcaattca ggcttctttg cttacttggt  46740
gtctctagtt ctggtgcctg gtgctttggt caatgaagtg gggttggtag gattctatta  46800
cttacctgtt ttttggtttt attttttgtt ttgcagttct ccgggagatg ttgcataacc  46860
actccttcgt gggctgtgtg aatcctcagt gggccttggc acagcatcaa accaagttat  46920
accttctcaa caccaccaag cttaggtaaa tcagctgagt gtgtgaacaa gcagagctac  46980
tacaacaatg gtccagggag cacaggcaca aaagctaagg agagcagcat gaggtagttg  47040
ggagggcaca ggctttggag tcagacacat gtggtttcaa atccaagttc gaccatttcc  47100
catttatttg actgtagaca agttacattc ctaaactatg tctcagattt ctcatctgta  47160
agttgtggta ttactagtta acatgcaggg gttttgtttg tttgtttgtt tgtttgtttg  47220
tgagggtaag aaataaccca agaagcctag tccttggtag ttgctcagtg ccctataaat  47280
gttgtgaacc aggtggtgag ggtttggtgc tgctagagaa ttctggtatc tgctctgtgc  47340
aacagagtac tgtaggtgat gcaagagaaa gaagacctga tgccttcttt cctcccagct  47400
ttgagaatgg agcaaaggcc taccccagcc accaagtgag ccagtgggct tgatcagcac  47460
aggaaaggtg accccggcag tttcatttga ctattgcatg gctggcaaca tttctattga  47520
ttgtttccag ggaccttggc ggatgagctc ctgttgagtc tagcatctct gttaaatctg  47580
ttctcaaata ggtaatgcat atgggaggat gctgccacct tgcatctact agacatcacc  47640
tatctactgt gagactctcc ctctaagccc tgctgtggcc tcagagtgct tattggccct  47700
gtgagtgggg cagccactat acattgcatg gagttggtac atgagataga aacctattcg  47760
ccatcccttg aaactgcccc agtccagaag cttcctgtta gcacatgtac ctccttgtat  47820
gtattcagaa ctcattccat ttaggcttgg aaacccgttt ggtgcaactc tgttcaagtt  47880
ccattgtctg ctttgagaat gcttgggctt gtatagtgag ctgtcacttt ttaatttgtt  47940
aggaattcta ctcgccttgc tttttctttt ccagcatgtt taagggaatg acctccaagg  48000
ccccaaatca cagttgtatt catgttcttt catttcacag atacaatcca ggccagtccc  48060
agatttgcag ctgttaataa atgtgaatgg ttttccagta agggggtaga aaaacatagg  48120
gagagaaccg ggttcagagt tcaatatctg gattcaagtc cttcctttag cactttacta  48180
actgatgtag aataagtcag ctactcaata ggtgcctcag tttccccacc aaaatgcaga  48240
catagaaggt gctttgtctg ctttgatgag aagtctttaa gcaagtctat ggggttcaat  48300
gtgttttaag aactataaag taccatataa atgtggcctt tattcccatt gtgttcttgg  48360
aagtaattca atatagtgtg tacttcatag ctgcttttgg actattgcca gccagtgtat  48420
catcctaaac tacatgtcag catagtataa tcctgcctta ggtctacttt tgattattta  48480
ggaagactcc ctgcccttcc tatacatttc acataatttt taataagttg taaaaaagtg  48540
atttatagga ttctttgtaa gtgggggaag ttaagcagac aaaaagtttt taaatcttac  48600
```

```
tgcagagtgt caggaacctt ttatagcacc agacaggtag ggacagaaca tgagtggcag  48660
caagccagac ttggtcttag tgctctaacc tgtctgttag aggctggcca gtcagacccc  48720
tggttgaaga cgttgggaat cccagctctt tggaggggta agagattttg ttagactgtt  48780
aaccagattc cacagccagg cagaactatt tctgtctcat ccatgtttca gggattactt  48840
ctcccatttt gtcccaactg gttgtatctc aagcatgaat tcagcttttc cttaaagtca  48900
cttcattttt attttcagtg aagaactgtt ctaccagata ctcatttatg attttgccaa  48960
ttttggtgtt ctcaggttat cggtaagttt agatcctttt cacttctgaa atttcaactg  49020
atcgtttctg aaaatagtag ctctccacta atatcttatt tgtagtatgt taaatttttc  49080
taaaacttct aaggatagtt gctgtattgt atgatttgca tatggaggta tctataagaa  49140
gttttatact ttttagcaaa atagtcattt ggtagccaac ttaaacaaat gtttattaat  49200
atagaagtta ataatatcta ctgatactcg gccgggtgcg gtggctcatg cctgtaatcc  49260
caccactttg ggaggctgag gcgggcagat catttgaggt caggagttca agaccagcct  49320
gaccaatatg atgaaaccct gtctctacta aattacaaat attagcaggg tatggtggtg  49380
ggcgcctgta atcccagcta ctcaggaggc taaggcagga gaatcatttg aacccaggag  49440
gcagaggttg caatgagctg agatcacgcc actgcactcc agcctgggca acagagcaag  49500
attccctcaa aaaaataaat atctactgac acttaatact tggaaaggga taaaaataaa  49560
cattgtctaa agccgtggtc caaacacaac ccctgccaac aattttagtc catttcttcc  49620
aagacttttt tttttctatg ccttttgtga aaactgtcaa aaactttttc aatgctgaat  49680
tttagttctg agttaaaaat catactacct gtttatatgg tttcatatcc actttttttca  49740
tgtgatatac tctacaaaaa gcctgctgag attttgattg ggattatgtt gaatctagat  49800
caatttaggg tgaaaaactt ttgttagata aatcccttag tatttcacat ttttaaatgc  49860
taaatggcat ttttcaaaaa ttttcttttt tcttttcttt tttgagacag agtcttgctc  49920
tgttgcccag gctggagtgc aatggcaaaa tcttggttca ctgcaacctc cgcctcctgg  49980
gttcaagcga ttctcaaact gcctcagcct cccaagtagc tgggattaca ggcatgtgcc  50040
accatgcccg gctaattttt taaactattt atagtagaga gggggtttca ccatgttggc  50100
caggctggtc ttgaactcct gacctcaggt gatctgccca ccttggcttc ccaaagtgct  50160
gggattacag gtgtgagcca ctgcacctgg cctcaaattt tttttttttt ttttttttaag  50220
agacaggggt ctcactcttg cctaggctgg agtgcagtgg cgtgatcata ggtcactgaa  50280
gctttgaact cctaggctca agtagctagg aatacaagtg tgtaccacta cacctggcta  50340
attttttttaa aaaaattttt ttcgtagaaa cgggagtctt gtgttaccaa ggctaatctc  50400
aaactcatgg cctcaagtga tactcttgcc tcagcctccc agagtgctag gattgtaggc  50460
atgagttact tcacccagcc aaaaaacttc aatttcctat tgtttatttg ctagtatata  50520
gaaatacata tagttttgta ccttgatgct gtatcttgca accttgttaa actcacttac  50580
tagttctagt atatttttttg tagattctat cagattttct atatatgtat catgtcttct  50640
gagaataaag aaacttttac ttcttgctgt gcaaactgaa cacctttttct ttctttcttt  50700
cttttttttaa gacggagttt tgctcttgtc acccaggctg gagtgcagtg gctggatctc  50760
ggcttactgc aacctccacc tcctgggttc aggcaattct cctgcctcag cctcctgagt  50820
agctgggatt acaggcgctc gccaccacgc ccggctaatt tttttgtatt tttagtagag  50880
atggggtttc accatgtggc cgagctggtc ttgaactcct gacctcaggt aatctgcttg  50940
tctcggcctc ccaaagtgct gggattacag gcgtgaatta ctgcgcccgg ctgcctttta  51000
```

```
tttctttctc ttgactgact gcactggcta gagcctccaa tacaatgttg aatagaagtg  51060
gtaagaatgg gccaggcatg gtggctcatg cctctaatcc tagcactttg ggagagtatg  51120
gtgggcaggt tacttgaggc caggagtttg agatcagcct ggcgaacatg gtgaaactct  51180
gtctctatta aaaatacaaa atatagttgg gtgtggcagt tcacgtctgt aatcccagct  51240
acttgggtgg ctgaggcatg agaatcactt gaacccagga ggcggaggtt gcagtgagcc  51300
aagaatgcac cactgcactc cagcctgggc aacacacaca cacacgaaaa acgaagtggt  51360
aaggatggaa atccttctct tcttcctgat ctaaggggga aaggggaaag ttacaaaaca  51420
ttcagtatgc tgttagccat ataggttttt ttgtagatgc ccattatgag gttgaggaag  51480
ttccctctgt tccttatttg ctacagattt tatttaggat tggatgttga atttttttca  51540
aatgcttttt ttgcatctac tgagataatc atatgatttt tcttttatag tttgttaata  51600
tagtgaatta cattgatttt cttatgttaa accaatcttt gcattcctgg gatgaactct  51660
gcttggttat aatatataat cctttttatt tattatggga tttgatttgc taaaattttt  51720
attataatta ttttatctgt gctcatgatt gttactagtt tatagttttc ttttagtctt  51780
tggtttttgt atcagggtaa tgctggcctc atagaatgag ttggtaagta tcccctcctt  51840
ttccattttc tgaaagagtt ttgtgtagaa ttgatgttaa aattattgct taatgtttgg  51900
cagaactcaa cagtgaagcc atctgggctt ggagattttc ttcatgggaa ggtttttaac  51960
tgcaaattct atttctttaa tagtatagag ctattcaggt tatctgtttc ttcttaggta  52020
agctttggta ttttgtttct ttgaagaaat ttgtcgcatt taatctaaat ttttaaattt  52080
actgacataa agttatttat aatatttctt attcttttat tatctatgga tctcttggtg  52140
acataacctc tctcattcct aatattggta atttcaggct tttcttttta acttggtcag  52200
tctggctaga ggtttatcaa ttttattgat cttctcaaag aactaacttt tggtttcata  52260
gatttttcta ttttctattt cattgatatc tgctctgact tttaatcttt cttataccta  52320
ttttggttta atttgtcttc tgtttcacat ttcttttttt tttttttttt tttttttga  52380
gacagagtct tgctctgtcg cccaggctgg agtgcagtac agtggtgcga tcttggctca  52440
ctgtaacctc agccttccag gttcaagcga ttcctgtttc taagcctccc aagtagctga  52500
gattacaggc atgcaccacc agctaatttt tgtattttta gtagagatgg ggtttcactg  52560
tgttggccag gctggtctca aactcctgac ctcaggtgat ccacctgcct tggcctccca  52620
gagtgctggg attacaggtg tgagccactg tggctggcct gtttcacatt tcttaaggta  52680
gaagctgagg tcacggattt gagacctttc ttcttttcta atacaggtgt taagtgctac  52740
aaatatccct taagcactgc ttcaacagca tcccacaaat tttgatagtt tgttttcatt  52800
ttcattcagt tcaaaatacc ttctaatttc ccttttgatt tcgtctttga cctacaggtt  52860
ttttagaact gtgttattta gtttccaatc tcttgaggat ttttaaaaca atatgttatt  52920
gatttctaat ttatttccat ctcagtcaaa gaacatactt gccttttttt atacatttat  52980
tgaaactttt tttatggccc agaatatggt ctgtgttggt aaatgttcca tgtgtacttg  53040
aaaataattt gtattctgat ctcattgagt tgaatgttct aggtatatca agttgatagt  53100
gatgcccaag tctcctgtat ctttactgat tttctgcctg ttctgttatt gagaaagggg  53160
tattgaaact tccaactata attatgattt gtctgttctc tttgcagttc tcttagtttt  53220
tgccttcata tatatataca tatatatgta tatatatata tatttttttt tttttgagat  53280
ggagtcttgc tctgttgccc aggctggagt gcagtggtgt gatcttggct cactgcaagc  53340
```

```
tccgcctccc aggttcacgc cattctcctg cctcagcctc ccgaatagct gggactacag  53400
gcgcccacca ccacgcccag ctaatttttt gtatttttag tagagacagg gtttcaccat  53460
gttagcaagg atggtctcga tctgacctcg tgatccgccc agcttagcct cccaaagtgc  53520
tgggattaca ggcatgagcc actgcaccca gcccatatat tttaaagctc tgttattggg  53580
tacataaaca tttaggattg ttatatcctt ttgataatgg actcttctat tatgaaaaga  53640
taatatactg tgggtttata acatatgtaa aagtatgagt aacatattat cagaagggga  53700
gaaatggaag ataacttagg catcttattt ttaagcatag ttttcccttt gtttctgcat  53760
tagatgattt acctgaaatg tcattcaatt taacttactc tccatcctca cccgcccagc  53820
tttggttatg aggcagtaga aagaaatgat ctgcctgtgg ttttctagaa atacgaaagt  53880
tgagtcctta aggctacaca gaaagaaagt acctccccag ggcttcaccc ttcccatcct  53940
ttcagcaggc tttttgtctg tcgtatcttc tctgttgaaa tggccattga caagaggagg  54000
aaaggggttt tgttgtggat tgttcaggca cttcctttgg ggtatatggg ggatgagtgt  54060
tacatttatg gtttctcacc tgccattctg atagtggatt cttgggaatt caggcttcat  54120
ttggatgctc cgttaaagct tgctccttca tgttcttgct tcttcctagg agccagcacc  54180
gctctttgac cttgccatgc ttgccttaga tagtccagag agtggctgga cagaggaaga  54240
tggtcccaaa gaaggacttg ctgaatacat tgttgagttt ctgaagaaga aggctgagat  54300
gcttgcagac tatttctctt tggaaattga tgaggtgtga cagccattct tatacttctg  54360
ttgtattctt caaataaaat ttccagccgg gtgcggtggc tcatggctgt aatcccagca  54420
ctttgggagg ctgaggtggg cagataactt ggggtcagga gttcaaaacc agctggccaa  54480
catgatgaaa ccccgtctct actaaaaaaa tagaaaaatt agccaggcgt ggtggcgggt  54540
acctgtaatc caagctgctc aggaggctga ggcagaagaa tcacttaaac ccaagaggta  54600
gaagttgcag tgagccgaga ttgcaccact gcactctagc ctaggcgaca gcgagactgc  54660
gtctcaaaaa aaaaaaaaaa gaacgttcca aggtcaggac taggcctccc ctcagaagca  54720
gcaagtgaca tatgtgacat cctctccact ccctatttgc atttctaggt tatataactg  54780
tactactatc catgcatgcc tactcttgtt cccagggtga aggacccaga catggagagc  54840
cgaatccctg caggccatta taaatgagat tatgccattt gctcccattt cttcttattc  54900
tttcattttt ggggctctcc atcttgatgt gttctttgga tcgtgaacag atccaaagaa  54960
aaggttgttc tgccgtgctg tttgtcagga tgaaaaactc ttttttaagt gtttaggtct  55020
gcccccagtg cccagcccaa tcaagtaacg tggtcaccca gagtggcaga taggagcaca  55080
aggcctggga aagcactgga gaaatgggat ttgtttaaac tatgacagca ttatttcttg  55140
ttcccttgtc ctttttcctg caagcaggaa gggaacctga ttggattacc ccttctgatt  55200
gacaactatg tgccccccttt ggagggactg cctatcttca ttcttcgact agccactgag  55260
gtcagtgatc aagcagatac taagcatttc ggtacatgca tgtgtgctgg agggaaaggg  55320
caaatgacca ccctttgatc tggaatgata aagatgataa gggtgggata gctgaaggcc  55380
tgctctcatc cccactaata ttcattccca gcaatattca gcagtcccat ttacagtttt  55440
aacgcctaaa gtatcacatt tcgtttttta gctttaagta gtctgtgatc tccgtttaga  55500
atgagaatgt ttaaattcgt acctattttg aggtattgaa tttctttgga ccaggtgaat  55560
tgggacgaag aaaaggaatg ttttgaaagc ctcagtaaag aatgcgctat gttctattcc  55620
atccggaagc agtacatatc tgaggagtcg accctctcag gccagcaggt acagtggtga  55680
tgcacactgg caccccagga ctaggacagg acctcataca atctttagga gatgaaactt  55740
```

```
gcccatctct aaaatttcgg gatttctttg tacccaacaa ggttcaaaca caacagtcag  55800

cttttattca tgatttttac ttccatctgc tgatgtagaa catacctcca gagtgacctc  55860

agaaattgtc aaatgtgaaa acacaagcca tcacagtgag aaatgggagg ttgagttaga  55920

ttgtctaagg ctggagagtc catatactcc cactgttagc tctgaagtgt gtagccagtc  55980

ttcagattct gggtcagttg cctcagtctc tcttagcttt tgccttactc tttatccgac  56040

cactgccctg ccaggaaaac aaggctctat aactcctctt acaggtcagc ttgacacaaa  56100

aagggtgcct ggattcctaa tgtttcattg tcacttttcc cagtcagatg ataatgcttt  56160

tcaaatcaac atatattttg ggggaggttg gaagggagag ttgaaatatt ctaagaatca  56220

aagagtagcc cactttaatc agagtatgac ccctgattgc tcacagtcat ctcctgagca  56280

gtgtgagcga gtttcagatg aggaggctga aggccagtca ggcatgctcg aggattccaa  56340

gtctgtaggt gggagggcag agatttagtc ctgttggcca aagcctctag ggaatttctc  56400

actccagtgg agaaggcaac acacttacca aactgtgtgg aaactatctc atttgattag  56460

aaattttacc tcaagaagag gaaggacagt tgagaaagaa cattttctta cacatgagac  56520

agctaaggct tacaagaagg agaggaataa tgaggcaaaa taatcctcat taatattttc  56580

attcctcccc tggggattag aactactttc agacccgatt ttaatggtaa gttaggtact  56640

tcctacagtt gccatccaaa tatcagtcag gatcagacat gatgttagct cctgctacaa  56700

taaaaccatt ttctccctga atgaaaacaa aggttccaca ggagacagtc ccacagagca  56760

gtggcttctt ttcctccctt taaaacctca tgttggctgg acacagtggc tcacacctgt  56820

aatcccagca ttttaggagg ctgaggtggg aagatggctt aagcccagga gtttgaggct  56880

gtagagctat gatcacacca ctgcccttca gcctgggtga cagagcaaga ccttgtctct  56940

aaataaacaa acaaacaaaa aatcctcttg tgttcaggcc tgtgggatcc cctgagaggc  57000

tagcccacaa gatccacttc aaaagcccta gataacacca agtctttcca gacccagtgc  57060

acatcccatc agccaggaca ccagtgtatg ttgggatgca aacagggagg cttatgacat  57120

ctaatgtgtt ttccagagtg aagtgcctgg ctccattcca aactcctgga agtggactgt  57180

ggaacacatt gtctataaag ccttgcgctc acacattctg cctcctaaac atttcacaga  57240

agatggaaat atcctgcagc ttgctaacct gcctgatcta tacaaagtct ttgagaggtg  57300

ttaaatatgg ttatttatgc actgtgggat gtgttcttct ttctctgtat tccgatacaa  57360

agtgttgtat caaagtgtga tatacaaagt gtaccaacat aagtgttggt agcacttaag  57420

acttatactt gccttctgat agtattcctt tatacacagt ggattgatta taaataaata  57480

gatgtgtctt aacataa                                                57497
```

<210> SEQ ID NO 3
<211> LENGTH: 2662
<212> TYPE: RNA
<213> ORGANISM: Homo sapiens

<400> SEQUENCE: 3

```
gaagagaccc agcaacccac agaguugaga aauuugacug gcauucaagc uguccaauca     60

auagcugccg cugaagggug gggcuggaug gcguaagcua cagcugaagg aagaacguga    120

gcacgaggca cugaggugau uggcugaagg cacuuccguu gagcaucuag acguuuccuu    180

ggcucuucug gcgccaaaau gucguucgug gcaggggua uucggcggcu ggacgagaca    240

guggugaacc gcaucgcggc gggggaaguu auccagcggc cagcuaaugc uaucaaagag    300
```

-continued

```
augauugaga acuguuuaga ugcaaaaucc acaaguauuc aagugauugu uaaagaggga    360
ggccugaagu ugauucagau ccaagacaau ggcaccggga ucaggaaaga agaucuggau    420
auuguaugug aaagguucac uacuaguaaa cugcaguccu uugaggauuu agccaguauu    480
ucuaccuaug gcuuucgagg ugaggcuuug gccagcauaa gccauguggc ucauguuacu    540
auuacaacga aaacagcuga uggaaagugu gcauacagag caaguuacuc agauggaaaa    600
cugaaagccc cuccuaaacc augugcuggc aaucaaggga cccagaucac gguggaggac    660
cuuuuuuaca acauagccac gaggagaaaa gcuuuaaaaa auccaaguga agaauauggg    720
aaaauuuugg aaguuguugg cagguauuca guacacaaug caggcauuag uuucucaguu    780
aaaaaacaag gagagacagu agcugauguu aggacacuac ccaaugccuc aaccguggac    840
aauauucgcu ccaucuuugg aaaugcuguu agucgagaac ugauagaaau uggaugugag    900
gauaaaaccc uagccuucaa aaugaauggu uacauaucca augcaaacua cucagugaag    960
aagugcaucu ucuuacucuu caucaaccau cgucugguag aaucaacuuc cuugagaaaa   1020
gccauagaaa caguguaugc agccuauuug cccaaaaaca cacacccauu ccuguaccuc   1080
aguuuagaaa ucagucccca gaauguggau guuaaugugc accccacaaa gcaugaaguu   1140
cacuuccugc acgaggagag cauccuggag cgggugcagc agcacaucga gagcaagcuc   1200
cugggcucca auuccuccag gauguacuuc acccagacuu ugcuaccagg acuugcuggc   1260
cccucugggg agaugguuaa auccacaaca agucugaccu cgucuucuac uucuggaagu   1320
agugauaagg ucuaugccca ccagauggau cguacagauu cccgggaaca gaagcuugau   1380
gcauuucugc agccucugag caaaccccug uccagucagc cccaggccau ugucacagag   1440
gauaagacag auauuucuag uggcagggcu aggcagcaag augaggagau gcuugaacuc   1500
ccagccccug cugaaguggc ugccaaaaau cagagcuugg agggggauac aacaaagggg   1560
acuucagaaa ugucagagaa gagaggaccu acuuccagca accccagaaa gagacaucgg   1620
gaagauucug auguggaaau gguggaagau gauucccgaa aggaaaugac ugcagcuugu   1680
accccccgga gaaggaucau uaaccucacu aguguuuuga gucuccagga agaaauuaau   1740
gagcagggac augagguucu ccgggagaug uugcauaacc acuccuucgu gggcugugug   1800
aauccucagu gggccuuggc acagcaucaa accaaguuau accuucucaa caccaccaag   1860
cuuagugaag aacuguucua ccagauacuc auuuaugauu uugccaauuu ugguguucuc   1920
agguuaucgg agccagcacc gcucuuugac cuugccaugc uugccuuaga uaguccagag   1980
aguggcugga cagaggaaga ugguccaaa gaaggacuug cugaauacau uguugaguuu   2040
cugaagaaga aggcugagau gcuugcagac uauuucucuu uggaaauuga ugaggaaggg   2100
aaccugauug gauuaccccu ucugauugac aacuaugugc cccuuugga gggacugccu   2160
aucuucauuc uucgacuagc cacugaggug aauugggacg aagaaaagga auguuuugaa   2220
agccucagua aagaaugcgc uauguucuau uccauccgga agcaguacau aucugaggag   2280
ucgacccucu caggccagca gagugaagug ccuggcucca uuccaaacuc cuggaagugg   2340
acuguggaac acauugucua uaaagccuug cgcucacaca uucugccucc uaaacauuuc   2400
acagaagaug gaaauauccu gcagcuugcu aaccugccug aucuauacaa agucuuugag   2460
agguguuaaa uaugguuauu uaugcacugu gggauguguu cuucuuucuc uguauuccga   2520
uacaaagugu uguaucaaag ugugauauac aaaguguacc aacauaagug uugguagcac   2580
uuaagacuua uacuugccuu cugauaguau uccuuuauac acaguggauu gauuauaaau   2640
aaauagaugu gucuuaacau aa                                            2662
```

<210> SEQ ID NO 4
<211> LENGTH: 2271
<212> TYPE: DNA
<213> ORGANISM: Homo sapiens

<400> SEQUENCE: 4

```
atgtcgttcg tggcaggggt tattcggcgg ctggacgaga cagtggtgaa ccgcatcgcg     60
gcgggggaag ttatccagcg gccagctaat gctatcaaag agatgattga gaactgttta    120
gatgcaaaat ccacaagtat tcaagtgatt gttaaagagg gaggcctgaa gttgattcag    180
atccaagaca atggcaccgg gatcaggaaa gaagatctgg atattgtatg tgaaaggttc    240
actactagta aactgcagtc ctttgaggat ttagccagta tttctaccta tggctttcga    300
ggtgaggctt tggccagcat aagccatgtg gctcatgtta ctattacaac gaaaacagct    360
gatggaaagt gtgcatacag agcaagttac tcagatggaa aactgaaagc ccctcctaaa    420
ccatgtgctg gcaatcaagg gacccagatc acggtggagg acctttttta caacatagcc    480
acgaggagaa aagctttaaa aaatccaagt gaagaatatg ggaaaatttt ggaagttgtt    540
ggcaggtatt cagtacacaa tgcaggcatt agtttctcag ttaaaaaaca aggagagaca    600
gtagctgatg ttaggacact acccaatgcc tcaaccgtgg acaatattcg ctccatcttt    660
ggaaatgctg ttagtcgaga actgatagaa attggatgtg aggataaaac cctagccttc    720
aaaatgaatg gttacatatc caatgcaaac tactcagtga agaagtgcat cttcttactc    780
ttcatcaacc atcgtctggt agaatcaact tccttgagaa aagccataga aacagtgtat    840
gcagcctatt tgcccaaaaa cacacaccca ttcctgtacc tcagtttaga aatcagtccc    900
cagaatgtgg atgttaatgt gcaccccaca aagcatgaag ttcacttcct gcacgaggag    960
agcatcctgg agcgggtgca gcagcacatc gagagcaagc tcctgggctc caattcctcc   1020
aggatgtact tcacccagac tttgctacca ggacttgctg gcccctctgg ggagatggtt   1080
aaatccacaa caagtctgac ctcgtcttct acttctggaa gtagtgataa ggtctatgcc   1140
caccagatgg atcgtacaga ttcccgggaa cagaagcttg atgcatttct gcagcctctg   1200
agcaaacccc tgtccagtca gccccaggcc attgtcacag aggataagac agatatttct   1260
agtggcaggg ctaggcagca agatgaggag atgcttgaac tcccagcccc tgctgaagtg   1320
gctgccaaaa atcagagctt ggagggggat acaacaaagg ggacttcaga aatgtcagag   1380
aagagaggac ctacttccag caaccccaga aagagacatc gggaagattc tgatgtggaa   1440
atggtggaag atgattcccg aaaggaaatg actgcagctt gtaccccccg gagaaggatc   1500
attaacctca ctagtgtttt gagtctccag gaagaaatta atgagcaggg acatgaggtt   1560
ctccgggaga tgttgcataa ccactccttc gtgggctgtg tgaatcctca gtgggccttg   1620
gcacagcatc aaaccaagtt ataccttctc aacaccacca agcttagtga agaactgttc   1680
taccagatac tcatttatga ttttgccaat tttggtgttc tcaggttatc ggagccagca   1740
ccgctctttg accttgccat gcttgcctta gatagtccag agagtggctg gacagaggaa   1800
gatggtccca aagaaggact tgctgaatac attgttgagt ttctgaagaa gaaggctgag   1860
atgcttgcag actatttctc tttggaaatt gatgaggaag ggaacctgat tggattaccc   1920
cttctgattg acaactatgt gcccccttgg gagggactgc ctatcttcat tcttcgacta   1980
gccactgagg tgaattggga cgaagaaaag gaatgttttg aaagcctcag taaagaatgc   2040
gctatgttct attccatccg gaagcagtac atatctgagg agtcgaccct ctcaggccag   2100
```

-continued

```
cagagtgaag tgcctggctc cattccaaac tcctggaagt ggactgtgga acacattgtc   2160

tataaagcct tgcgctcaca cattctgcct cctaaacatt tcacagaaga tggaaatatc   2220

ctgcagcttg ctaacctgcc tgatctatac aaagtctttg agaggtgtta a            2271


<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5

cagactttgc taccaggact tgc                                             23


<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6

ctgcctagcc ctgccactag                                                 20


<210> SEQ ID NO 7
<211> LENGTH: 24
<212> TYPE: DNA
<213> ORGANISM: Homo sapiens

<400> SEQUENCE: 7

accagatgga tcgtacagat tccc                                            24


<210> SEQ ID NO 8
<211> LENGTH: 24
<212> TYPE: DNA
<213> ORGANISM: Homo sapiens

<400> SEQUENCE: 8

accagatgga tcgtacagat tccc                                            24
```